(12) United States Patent
Kim et al.

(10) Patent No.: US 10,502,724 B2
(45) Date of Patent: Dec. 10, 2019

(54) ULTRA-LOW POWER DIGITAL CHEMICAL ANALYZERS

(71) Applicant: University of Utah Research Foundation, Salt Lake City, UT (US)

(72) Inventors: Hanseup Kim, Salt Lake City, UT (US); Carlos Mastrangelo, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 310 days.

(21) Appl. No.: 15/376,562

(22) Filed: Dec. 12, 2016

(65) Prior Publication Data

US 2018/0231514 A1  Aug. 16, 2018

Related U.S. Application Data

(60) Provisional application No. 62/284,929, filed on Oct. 13, 2015.

(51) Int. Cl.
*G01N 33/00* (2006.01)
*G01N 27/02* (2006.01)
(Continued)

(52) U.S. Cl.
CPC ........... *G01N 33/0057* (2013.01); *A62D 3/11* (2013.01); *B01D 46/0032* (2013.01);
(Continued)

(58) Field of Classification Search
None
See application file for complete search history.

(56) References Cited

U.S. PATENT DOCUMENTS 7,075,428 B1 * 7/2006 Oleynik ........... G01N 33/54373
340/539.26
8,468,872 B2   6/2013 Lee et al.
(Continued)

FOREIGN PATENT DOCUMENTS

CN       1727889 A    2/2006
CN     103091370 A    5/2013
(Continued)

OTHER PUBLICATIONS

Arshak et al, "A Review of Gas Sensors Employed in Electronic Nose Applications." Sensor Review; Emerald; 2004; vol. 24, Issue 2; pp. 181-198.
(Continued)

*Primary Examiner* — Matthew D Krcha
(74) *Attorney, Agent, or Firm* — Thorpe North & Western, LLP

(57) ABSTRACT

A zero-power digital chemical analyzer can include a chemically-selective percolation switch. The chemically selected percolation switch can include a positive electrode and a negative electrode separated from the positive electrode by a gap. A binding agent can be located at binding sites in the gap. The binding agent can be selective for binding to a target chemical compound. The binding sites can be distributed in the gap so that target chemical molecules binding to the binding sites can form an electrically conductive pathway via a natural percolation phenomenon between the electrodes when the ambient concentration of the target chemical compound reaches a threshold concentration.

20 Claims, 24 Drawing Sheets

(51) Int. Cl.
    A62D 3/11      (2007.01)
    B01D 46/00     (2006.01)
    B82Y 40/00     (2011.01)
    B82Y 15/00     (2011.01)
(52) U.S. Cl.
    CPC ....... G01N 27/021 (2013.01); G01N 33/0063 (2013.01); *B01L 2300/0645* (2013.01); *B82Y 15/00* (2013.01); *B82Y 40/00* (2013.01)

(56) References Cited

U.S. PATENT DOCUMENTS

| | | | |
|---|---|---|---|
| 2003/0040179 A1 | 2/2003 | Fonash et al. | |
| 2008/0009002 A1* | 1/2008 | Gruner | B82Y 15/00 435/6.11 |
| 2009/0305432 A1* | 12/2009 | Liotta | B82Y 10/00 436/501 |
| 2010/0260745 A1 | 10/2010 | Zhou et al. | |
| 2012/0184045 A1 | 7/2012 | Toyoda | |
| 2015/0044428 A1 | 2/2015 | Oh et al. | |
| 2015/0233878 A1 | 8/2015 | Lee et al. | |
| 2015/0276643 A1 | 10/2015 | Striemer | |

FOREIGN PATENT DOCUMENTS

| | | | | |
|---|---|---|---|---|
| WO | WO-2014071566 A1 * | 5/2014 | ........... | G01N 27/125 |
| WO | WO 2014071566 A1 | 5/2014 | | |
| WO | WO 2014162148 A2 | 10/2014 | | |
| WO | WO 2015/026297 A1 | 2/2015 | | |

OTHER PUBLICATIONS

Chang et al, "Nanogaps Controlled by Liquid Nitrogen Freezing and the Effects on Hydrogen Gas Sensor performance." Sensors and Actuators A: Physical; Elsevier; Apr. 1, 2013; vol. 192; pp. 140-144.

Cho et al, "Ultrasensitive Detection of Toxic Cations Through Changes in the Tunneling Current Across Films of Striped Nanoparticles." Nature Materials; Macmillian; Sep. 9, 2012; vol. 11; pp. 978-985.

Doleman et al, "Use of Compatible Polymer Blends to Fabricate Arrays of Carbon Black-Polymer Composite Vapor Detectors." Anal. Chem; American Chemical Society; Jul. 1, 1998; vol. 70, Issue 13; pp. 2560-2564.

Fang et al, "Micro-Gas-Sensor With Conducting Polymer." Sensors and Actuators B:Chemical; Elsevier; Apr. 30, 2002; vol. 84, Issue 1; pp. 66-71.

Jang et al, "Nanogap-Based Electrical Hydrogen Sensors Fabricated From Pd-PMMA Hybrid Thin Films." Sensors and Actuators B: Chemical; Elsevier; Mar. 31, 2014; vol. 193; pp. 530-535.

Lee et al, "Highly Mobile Palladium Thin Films on an Elastomeric Substrate: Nanogap-Based Hydrogen Gas Sensors." Angewandte Chemie; Wiley; May 3, 2011; vol. 50; pp. 5301-5305.

Lee et al, "Pd—Ni Hydrogen Sponge for Highly Sensitive Nanogap-Based Hydrogen Sensors." International Journal of Hydrogen Energy; Elsevier; vol. 37, Issue 19; pp. 14702-14706.

Liu et al, "Host-Guest Interaction Dictated Selective Adsorption and Fluorescence Quenching of a Luminescent Lightweight Metal-Organic Framework Toward Liquid Explosives." Dalton Transactions; Royal Society of Chemistry; 2014; Issue 43; pp. 15237-15244.

Menumerov et al, "Sensing Hydrogen Gas From Atmospheric Pressure to a Hundred Parts Per Million With Nanogaps Fabricated Using a Single-Step Bending Deformation." ACS Sensors; American Chemical Society; Oct. 22, 2015; vol. 1, Issue 1; pp. 73-80.

Naitoh et al, "Effect of Gas Molecules on Resistance Switch Employing a Gold Nanogap Junction." Japanese Journal of Applied Physics; The Japan Society of Applied Physics; Jan. 20, 2010; vol. 49, Issue 1S; 3 Pages.

Sungyeon et al, "Strain-Controlled Nanocrack Formation in a Pd Film on Polydimethylysoloxane for the Detection of Low $H_2$ Concentrations." Journal of Materials Science; Springer; Feb. 2, 2016; vol. 51, Issue 9; pp. 4530-4537.

* cited by examiner

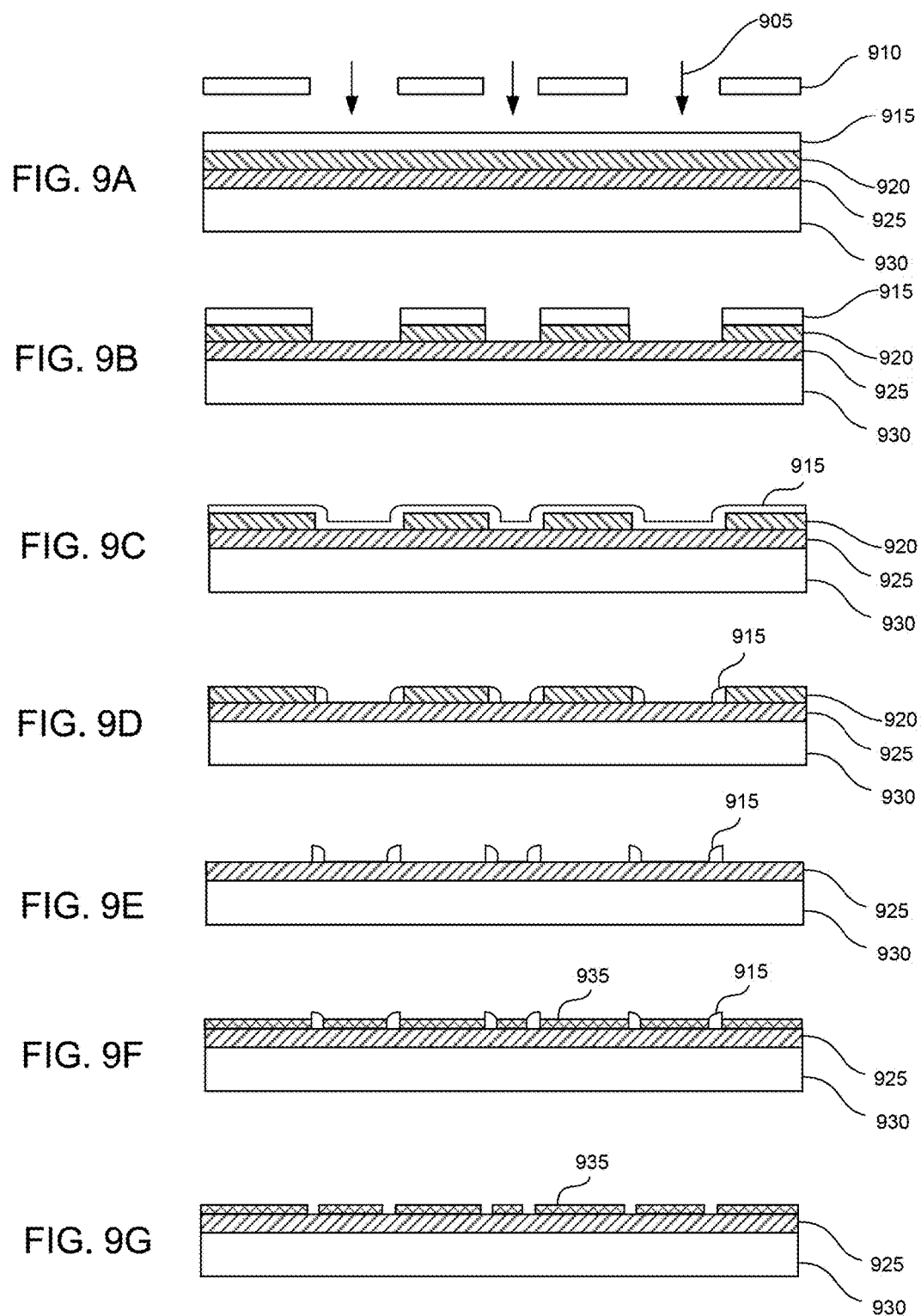

$R_{TA}(C_{TA})$ Capture on resistance (concentration dependent)

$R_{TU}$ Vacant off resistance $$R_{TA} \ll R_{TU}$$
$$R_L < R_{TA}$$

US 10,502,724 B2

ULTRA-LOW POWER DIGITAL CHEMICAL ANALYZERS

RELATED APPLICATION(S)

This application claims the benefit of U.S. Provisional Patent Application Ser. No. 62/284,929 filed on Oct. 13, 2015, which is incorporated herein by reference.

GOVERNMENT INTEREST

None.

BACKGROUND

At present, chemical sensors and electronic nose technology lack the capability of operating at sub-10 nW or nearly-zero power, which limits their distribution over a large area due to limited lifetime during battery operation. Existing chemical sensors and electronic nose technology can be categorized into four main groups, depending on their working principles: conductivity, piezoelectric, optical and field-effect-transistor (FET) sensors. FET sensors operate based on threshold voltage changes that are caused by the interaction of a gate material with certain gases, resulting in changes in work functions. Such work function changes occur due to polarization of the gate material surface and interface with catalysts (e.g. metal oxides) by target gases. To enhance such interaction and thus sensitivity, these sensors preferably operate at an elevated temperature between 50° C. and 170° C., which is not appropriate for some low-power applications. Optical sensors utilize a coating of fluorescence dyes around an optical fiber and measure the optical property changes, such as wavelength shifts. However, optical sensors typically require a continuously-power-consuming scheme of light sources and detectors, making the system too complex and inappropriate for many low-power applications. Piezoelectric sensors, such as surface acoustic wave (SAW) and quartz crystal microbalance (QCM) sensors, measure the shifts in frequency of acoustic waves caused by interaction with or mass of gas molecules that are captured in a gas sensitive membrane. To produce high-frequency (>1 MHz) vibration of the device, piezoelectric sensors inherently require high power consumption of greater than 100 µW. Conductivity sensors produce changes in conductance by interaction with a gas and a gas sensitive membrane and are further categorized into three groups, depending on the membrane material types: polymer composites (non-conductive), conducting polymers and metal oxides. Among these materials, metal oxides require high temperature to operate as gas sensors, typically 200° C. to 500° C., thus requiring high-power consumption. Both non-conductive and conductive polymers operate at room temperature and do not need an integrated heater or high power consumption. However, their 'off-current' is non-trivial, typically above 1 µA considering their resistance values between 1 kΩ and 1000 kΩ at an operation voltage of 1.0 V, which results in power consumption of greater than 1 µW. Most recent percolation-based chemical sensors operate in liquid with non-trivial off-power consumption of greater than 1 µW. Additionally these sensors rely on pattern recognition electronics to achieve target selectivity, which further precludes nearly zero-power operation, which is not appropriate for extended lifetime from a battery. In short, existing chemical sensors and electronic nose technology have not simultaneously achieved chemical selectivity and ultra-low power consumption with long battery lifetime.

SUMMARY

The present invention provides chemically-selective percolation switches and sensors incorporating such switches that can operate with zero or near-zero power consumption when a target chemical is present below a certain threshold concentration. In some examples, a chemically-selective percolation switch can include a positive electrode and a negative electrode separated from the positive electrode by a switch gap. A binding agent can be located at a plurality of binding sites in the switch gap. The binding agent can be selective for binding a target chemical compound. The binding sites can be distributed in the switch gap such that the binding sites are capable of binding molecules of the target chemical compound to form an electrically conductive pathway via percolation between the positive electrode and the negative electrode when the chemically-selective percolation switch is exposed to a threshold concentration of the target chemical compound.

In further examples of the present invention, a zero-power digital chemical analyzer can include a power supply, a detection circuit, and a chemically-selective percolation switch. The chemically-selective percolation switch can be electrically connected between the power supply and the detection circuit to switch the detection circuit to an on-state when the chemically-selective percolation switch is exposed to a threshold concentration of a target chemical compound. The chemically-selective percolation switch can include a positive electrode and a negative electrode separated from the positive electrode by a switch gap. A binding agent can be located at a plurality of binding sites in the switch gap. The binding agent can be selective for binding to the target chemical compound. The binding sites can be distributed in the switch gap such that the binding sites are capable of binding molecules of the target chemical compound to form an electrically conductive pathway via percolation between the positive electrode and the negative electrode when the chemically-selective percolation switch is exposed to the threshold concentration of the target chemical compound.

In still further examples of the present invention, a digital chemical analyzer can include a power supply, a first chemically-selective percolation switch, and a second chemically-selective percolation switch. The first chemically-selective percolation switch can be tuned to conduct electric current from the power supply when exposed to a first threshold concentration of a target chemical compound, and the second chemically-selective percolation switch can be tune to conduct electric current when exposed to a second threshold concentration. The second threshold concentration can be greater than the first threshold concentration or it can react to other target gases having its own threshold concentration. The first and second chemically-selective percolation switches can each include a positive electrode and a negative electrode separated from the positive electrode by a switch gap. A binding agent can be located at a plurality of binding sites in the switch gap. The binding agent can be selective for binding to the target chemical compound. The binding sites can be distributed in the switch gap such that the binding sites are capable of binding molecules of the target chemical compound to form an electrically conductive pathway via percolation between the positive electrode and the negative electrode when the chemically-selective percolation switch is exposed to the threshold concentration of the target chemical compound. These switches can be connected in parallel or in series. More than two switches can be connected in various combinations of parallel or series connections.

BRIEF DESCRIPTION OF THE DRAWINGS

FIGS. 9A-9G show steps in a method of fabricating nano-gap structures, in accordance with examples of the present invention.

Figure 1A:
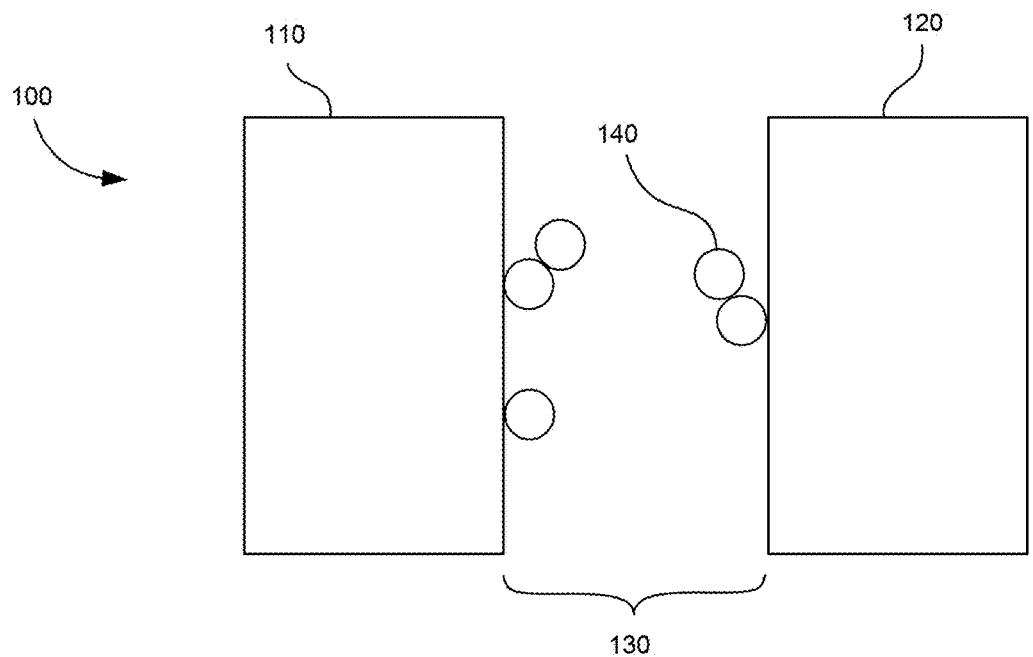
FIG. 1A is a schematic of a percolation switch in an "off" state, in accordance with examples of the present invention.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

It is noted that, as used in this specification and in the appended claims, the singular forms "a," "an," and "the" include plural referents unless the context clearly dictates otherwise. Thus, for example, reference to "an electrode" includes one or more of such materials and reference to "detecting" includes reference to one or more of such steps.

As used herein, the terms "about" and "approximately" are used to provide flexibility, such as to indicate, for example, that a given value in a numerical range endpoint may be "a little above" or "a little below" the endpoint. The degree of flexibility for a particular variable can be readily determined by one skilled in the art based on the context.

As used herein, the term "substantially" refers to the complete or nearly complete extent or degree of an action, characteristic, property, state, structure, item, or result. The exact allowable degree of deviation from absolute completeness may in some cases depend on the specific context. However, the nearness of completion will generally be so as to have the same overall result as if absolute and total completion were obtained. The use of "substantially" is equally applicable when used in a negative connotation to refer to the complete or near complete lack of an action, characteristic, property, state, structure, item, or result.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "percolation" and "chemical percolation" refer to the natural phenomenon of molecules of a target chemical compound forming an electrical connection between two electrodes when the target chemical compound is present above a certain threshold concentration. This phenomenon is described in more detail below. As used herein, "structure-assisted percolation" refers to the phenomenon of target chemical compound molecules forming an electrical connection in a switch gap where electrically conductive structures are present to assist in forming the electrical connection across the switch gap. As described in more detail below, electrically conductive structures can be placed in the switch gap to provide additional control over binding sites for the target chemical compound.

As used herein, "switch gap" refers to a gap between a positive electrode and a negative electrode of a chemically-selective percolation switch. In some examples, the switch gap can be substantially empty space. In other examples, the switch gap can contain electrically conductive structures.

As used herein, "structure gap" refers to a gap between adjacent electrically conductive structures within a switch gap. Thus, when multiple electrically conductive structures are present in a switch gap, the structures can be separated one from another by a structure gap. The structure gap distance is typically smaller than the switch gap distance. Furthermore, although in most cases structure gaps can be a uniform gap distance within a particular switch gap, the structure gaps and even shapes can be varied in some embodiments.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Examples of the Technology

Reference will now be made to the exemplary embodiments illustrated, and specific language will be used herein to describe the same. It will nevertheless be understood that no limitation of the scope of the technology is thereby intended. Additional features and advantages of the technology will be apparent from the detailed description which follows, taken in conjunction with the accompanying drawings, which together illustrate, by way of example, features of the technology.

With the general examples set forth in the Summary above, it is noted in the present disclosure that when describing the system, or the related devices or methods, individual or separate descriptions are considered applicable to one other, whether or not explicitly discussed in the context of a particular example or embodiment. For example, in discussing a device per se, other device, system, and/or method embodiments are also included in such discussions, and vice versa.

Furthermore, various modifications and combinations can be derived from the present disclosure and illustrations, and as such, the following figures should not be considered limiting.

The present invention provides chemically-selective percolation switches and sensors incorporating these switches. Such chemical sensors can 'sleep' when the ambient concentration of the target chemical compound is below a certain threshold, thus normally not consuming any power. The sensor can 'wake up' only in the event of introduction of the chemical target above a certain threshold concentration. In this way, the sensor can minimize the power consumption by substantially eliminating any static (or always-on) power consumption. This can dramatically extend the lifetime of the sensor by multiple orders of magnitude, thus greatly reducing the need for periodic battery replacement. Accordingly, the present disclosure is directed at chemically-selective percolation switches and digital chemical analyzers that incorporate the chemically-selective percolation switches. These devices introduce a new operation principle of a sensor that normally sleeps but can sense the introduction of chemical targets above a certain threshold concentration. This device uses the natural phenomenon of percolation. Percolation is a result of the natural process of multiple particles or molecules randomly forming an electrical connection within a switch gap. The switch gap is a space between a positive electrode and negative electrode in a switch according to the present invention. It has been found that a switch gap can be filled in various ways to form a connection between the electrodes. It has also been mathematically shown that a certain threshold concentration of particles is needed to result in percolation. This process does not require any power consumption because it is based on natural phenomenon. This invention provides sensors that can sense airborne target chemical compounds by utilizing the percolation phenomenon and a switch to wake up the sensor system above a certain target chemical concentration, thus consuming nearly-zero power normally when no or insufficient target chemical compounds are present.

FIG. 1A shows an example of a percolation switch 100 in an "off" state. In this example, a positive electrode 110 and a negative electrode 120 are separated by a switch gap 130. Target chemical molecules 140 are present in the switch gap. The target chemical molecules are constantly in motion, continuously bound to the sites only for a short period of time and then detached away, but in this example the concentration of the target chemical at a certain moment is not high enough to form an electrical connection across the switch gap (i.e. the concentration of target chemical is below the percolation limit).

Figure 1B:
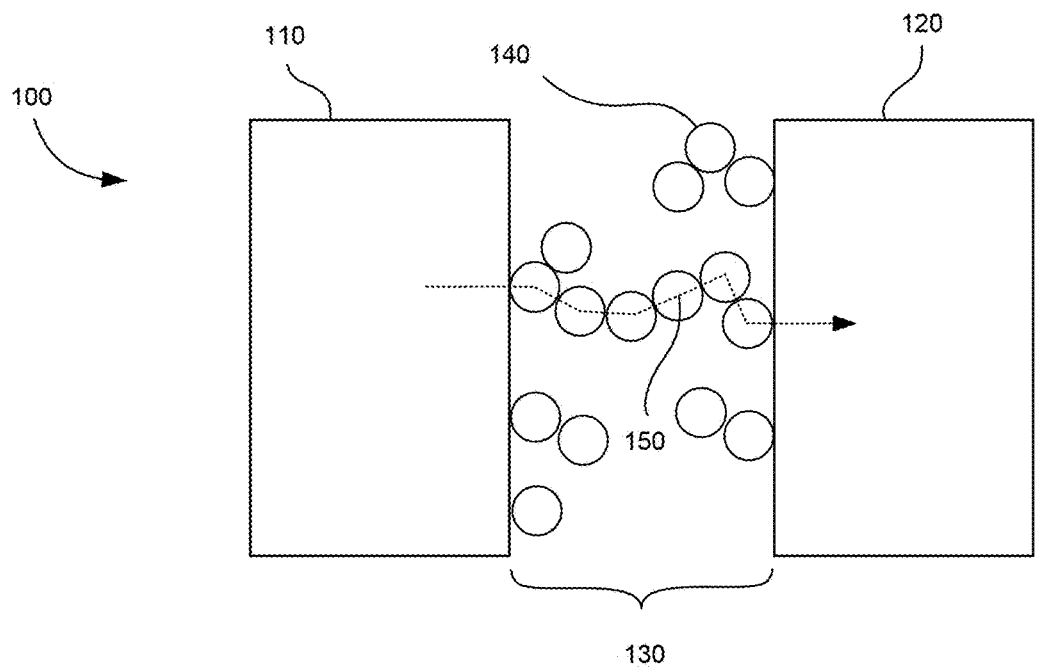
FIG. 1B is a schematic of a percolation switch in an "on" state, in accordance with examples of the present invention.

FIG. 1B shows the percolation switch 100 in an "on" state. When the target chemical concentration is above a certain threshold, the random movement of the molecules 140 results in a "bridge" forming across the switch gap 130. This creates an electrical connection that allows electric current 150 to flow between the positive electrode 110 and the negative electrode 120.

Figure 2:
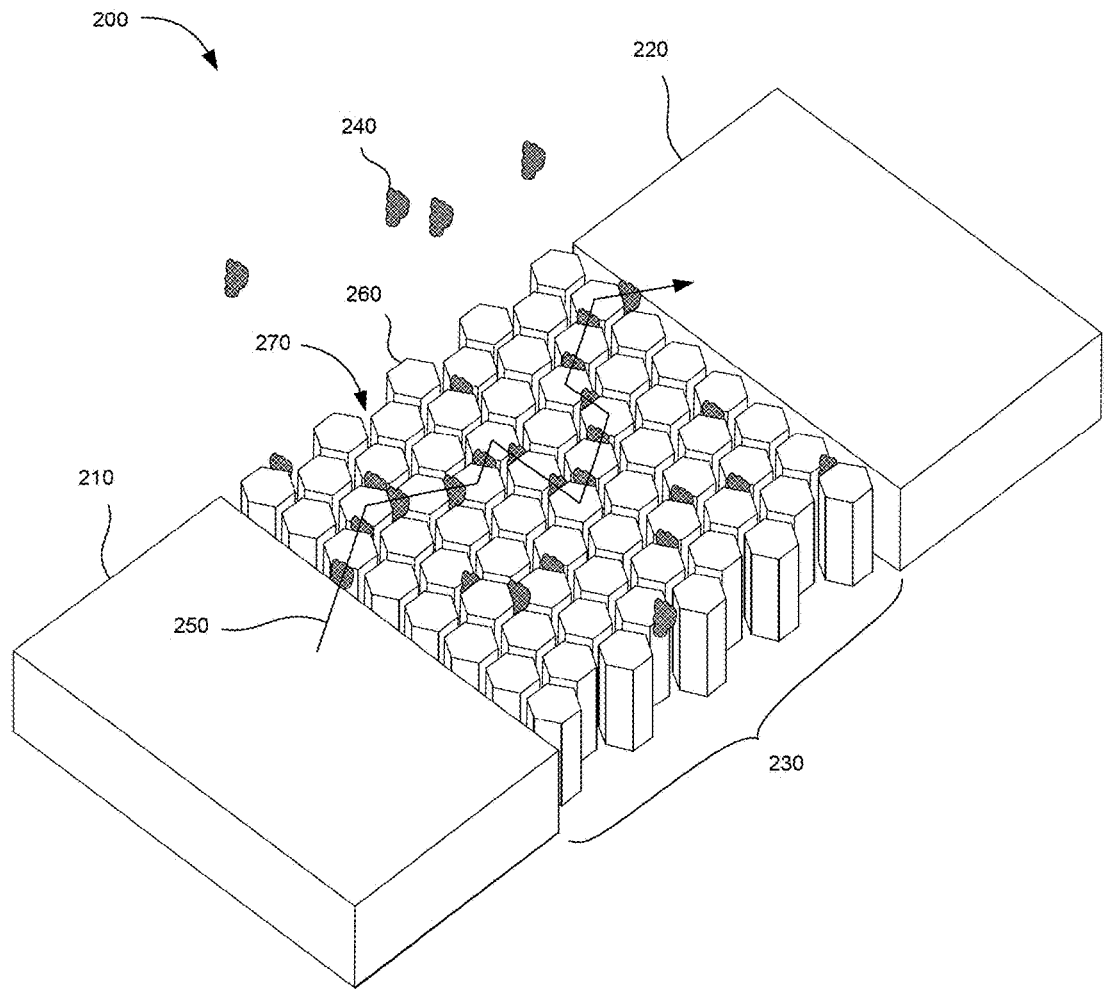
FIG. 2 is a schematic of a percolation switch including electrically conductive structures, in accordance with examples of the present invention.

FIG. 2 shows another example of a percolation switch 200, including a positive electrode 210 and a negative electrode 220 separated by a switch gap 230. In this example, electrically conductive structures 260 are located in the switch gap. In the particular example shown, the electrically conductive structures are in a form of hexagonal pillars. Each pillar is separated from adjacent pillars by a structure gap 270. In this example, the structure gap 270 is a uniform gap distance between each adjacent pillar throughout the switch gap 230. Target chemical molecules 240 can move into the structure gaps to form electrical connections between adjacent pillars. When a sufficient concentration of the target chemical is present, the molecules can form an electrical connection between the electrodes so that electric current 250 can flow. Thus, the percolation switch shown in FIG. 2 operates by structure-assisted percolation, a new type of percolation that involves electrically conductive structures within the switch gap to conduct electricity between the electrodes.

Because the target chemical molecules are constantly in motion, or only temporarily resides on the binding sites, the electrical connections formed by the molecules in the switch gap can be intermittent. In other words, an electrical connection formed by the random motion of molecules can be formed and last for a short period of time before one or more of the molecules moves away and breaks the connection. However, it has been found that when the surrounding concentration of the target chemical reaches a certain threshold, the molecules can tend to form electrical connections more often than not, so that the switch conducts electricity substantially constantly. Indeed, the current flowing through the switch can increase dramatically when the target chemical concentration rises above the threshold concentration.

Figure 3:
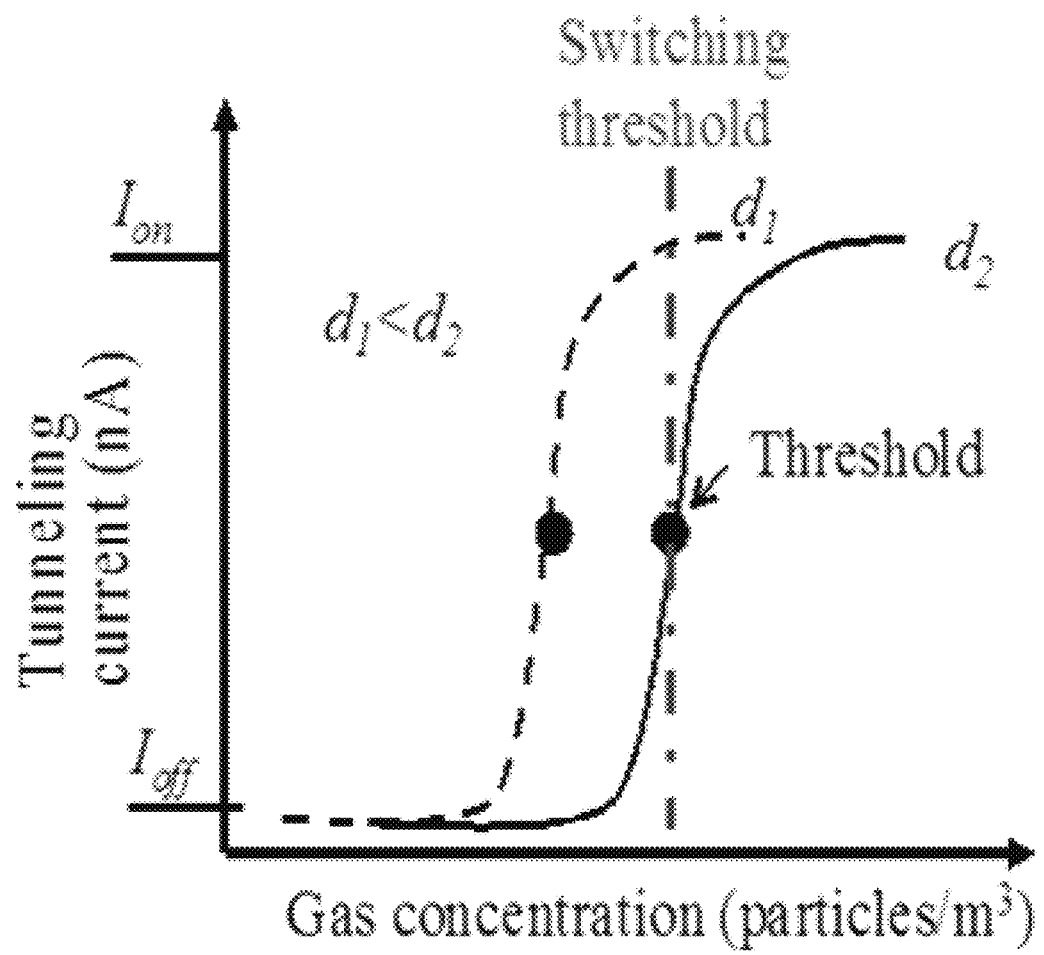
FIG. 3 is a qualitative graph showing the relationship between target chemical gas concentration and the electric current between electrodes of a percolation switch, in accordance with examples of the present invention.

FIG. 3 shows a qualitative representation of the relationship between target chemical gas concentration and the electric current between the electrodes of the percolation switch. Electric current travels across the switch gap by tunneling when the target chemical molecules form a sufficient bridge for tunneling to occur. The solid line represents the tunneling current in a switch with a switch gap distance $d_2$. When the gas concentration approaches the switching threshold, the tunneling current increases sharply. The dashed line represents the tunneling current of another switch having a switch gap distance $d_1$, where $d_1$ is less than $d_2$. As shown, in some cases reducing the switch gap distance or chemical residence time or binding site density can have the effect of reducing the switching threshold. Thus, switch gap distance is one parameter that can be adjusted to tune the switch to a particular desired threshold concentration. This same principle applies with the use of structure-assisted percolation such that structure gap distance, chemical residence time, binding site density, and additionally changing the configuration of connection sites through structure (i.e. square, rectangular, hexagonal, octagonal network, and even 3D structure heights) can be varied to manipulate a desired threshold concentration (e.g. sensitivity).

Figure 4A:
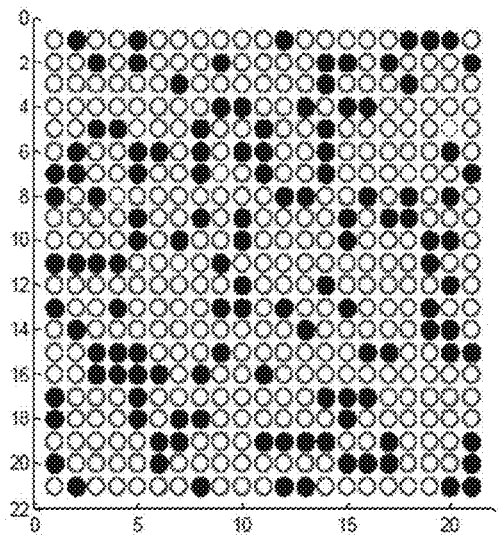
FIGS. 4A-4C are schematics of a mathematical model of percolation with various probabilities or concentrations of target chemical molecules occupying binding sites, in accordance with examples of the present invention.
Figure 4B:
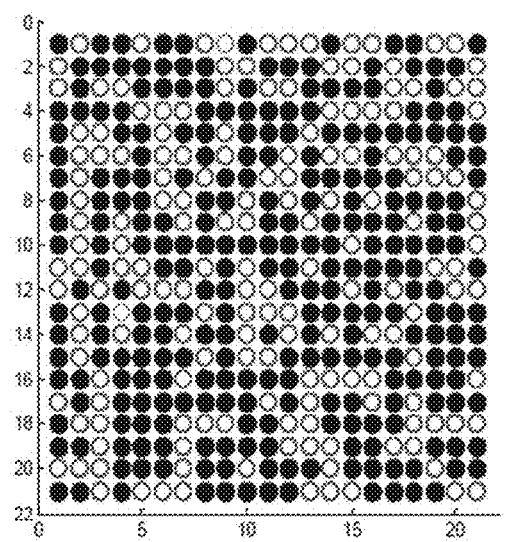
Figure 4C:
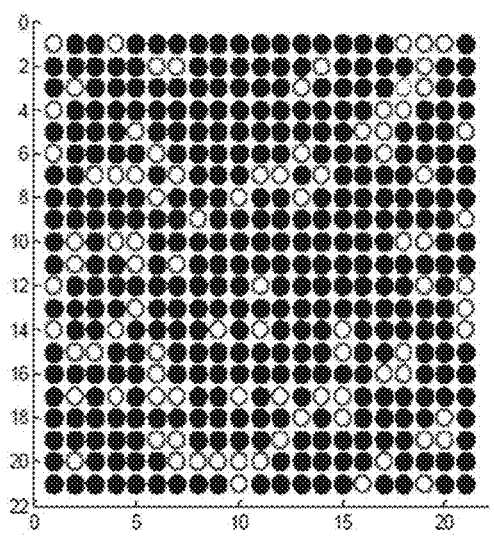

FIGS. 4A-4C show a statistical model of a percolation switch. Open circles represent binding sites without a target chemical molecule occupying the binding site. Solid circles represent target chemical molecules bound to a binding site. Under the normally-off state, molecules sparsely occupy the switch gap (FIG. 4A), and the spaces between the bound target chemical molecules remains too large for electron tunneling to occur, blocking current flow between the two electrodes and resulting in an ultra-low off-current, estimated as <1 pA. In the simulation shown in FIG. 4A, each binding site was modeled as having a probability of occupation $p=0.3$. In FIG. 4B, $p=0.55$ and in FIG. 4C, $p=0.85$.

Figure 5:
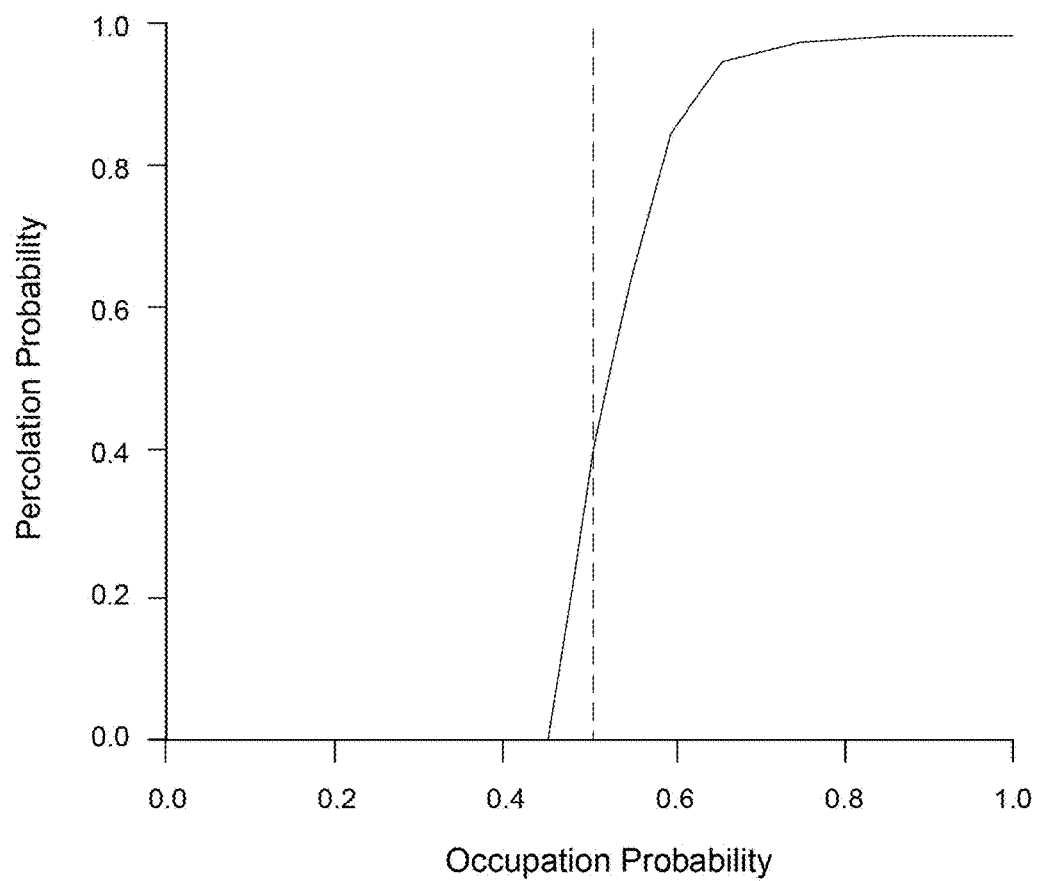
FIG. 5 is a graph of probability of percolation calculated using the mathematical model of FIGS. 4A-4C, in accordance with examples of the present invention.

FIG. 5 shows the probability of percolation (i.e., probability that electric current can flow through the switch gap) vs. the occupation probability p. The percolation probability remains substantially zero up to an occupation probability of 0.4-0.5, and then as the occupation probability rises to 0.5-0.6, the percolation probability sharply rises as well. In a real-life percolation switch, the occupation probability can be related to the concentration of the target chemical. Thus, when the target chemical concentration reaches a threshold concentration, the percolation probability and resulting electric current increase sharply.

When target chemical molecules become sufficiently available, the molecules will statistically adhere to the binding sites between the electrodes and form continuous paths for electron tunneling. However, this occurs only when the concentration is above a certain threshold. This phenomenon has been heavily modeled in mathematics, known as percolation theory. Various percolation models are available in 2D and 3D coordination. The simulations described herein use a site-percolation on a 2D Bethe lattice as the percolation model due to the similarities of molecular behaviors in the structure of the zero-power digital chemical analyzer. However, other 2D and 3D simulation models can be used such as, but not limited to, site percolation, bond percolation, Bernoulli percolation, Fortuin-Kasteleyn random cluster model, Potts models, directed percolation, first passage percolation, and the like. Corresponding lattice forms can include, but are not limited to, regular square grid, hexagonal grid, triangular grid, pentagonal grid, and the like. Note that the invention includes the possibility of including both 2D and 3D structure-assisted percolation by forming, i.e. hexagonal 2D gaps among conductive planar electrodes, or hexagonal 3D gaps among conductive pillar electrodes.

Simulation results predict a sharp transition between off and on states as shown in FIGS. 4A-4C and 5. Such a complete path allows electrons to travel across the gap due to the reduced distance between molecules being small enough, such as less than 0.1 nm, to result in significantly enhanced on-current and 'on-state' of the switch. On the nanometer scale, tunneling current can increase 10-fold with reduction of a gap by 0.1 nm.

Output digitization can be achieved in the chemically-selective percolation switch due to the characteristics of switching operation across a threshold, and the digitization threshold can be tuned by properly selecting the design parameters such as material properties and geometry. To be able to 'design' the digitization threshold values, a percolation prediction model can be devised by combining a percolation model algorithm with experimentally-obtained coefficients. Specifically, the established percolation model can consider the combinatory effects among adsorption periods of a molecule, binding site densities, a gap distance (i.e. both switch gap and structure gap), surface areas and molecular transportation in both 2D and 3D coordination. Particularly, gap distance control between the two electrodes is one of the design factors that can be used to manipulate threshold concentration.

An algorithm was developed by utilizing the Leath-Alexanderowicz method, to predict threshold and conduction probability. The probability distribution of growing cluster is described as $P(n, b) = m(n, \alpha) K n^{-x} (c/c_\alpha)^{n-1} [(1-c)/(1-c_\alpha)]^{\alpha n}$, where n is the number of sites, C is the target concentration, $C_a$ is the threshold concentration, and K, x are experimentally-adjusted constants, resulting in the percolation probability depending on target concentrations. The simulation results showed that a percolation threshold $p_c$ can be predicted in a normalized form to the total particle numbers required to completely fill the gap. Since the total particle number depends on electrode gap and width, binding site densities and adsorption (residence) period of the particle, the threshold concentration can be manipulated by controlling those parameters. For example, threshold concentration increases when the particle adsorption period decreases, the binding site densities decrease, and the electrode distance increases, thus allowing for threshold programming. Note that adsorption periods can also be adjusted by modifying binder properties, while binding site densities and electrode dimensions can be designed. Based on this algorithm, a percolation prediction model can be provided that is capable of providing design rules for a wide-range of percolation sensors, including electrode gap distances, structure gap distances, electrode widths, binding site densities and adsorption periods, by comprehensively incorporating the coefficients from the experimental data.

In various examples of the present invention, chemically-selective percolation switches can have a form as shown in FIG. 1A, 1B, or 2. In particular, in one example a chemically-selective percolation switch can have two electrodes separated by a switch gap that does not have any structures formed in the switch gap as shown in FIGS. 1A-1B. Alternatively, a chemically-selective percolation switch can include electrically conductive structures in the switch gap as shown in FIG. 2. In various examples, the switch gap can generally have a gap distance of 10 nanometers to 50 millimeters, while switch gap distances from about 20 nm to 10 mm can be particularly useful. In examples that include electrically conductive structures in the switch gap, the electrically conductive structures can generally be separated by a structure gap distance of 0.3 nanometers to 100 micrometers, and often from 5 nm to 100 μm depending on target molecule sizes and binding chemistry sizes. It is notable that depending on the sizes of target molecules and binding chemistry, the preferred gap distance to detect a particular molecule will vary. For example, if a binding molecule holds a length of 2 nm, the corresponding chemical molecules holds a length of 0.8 nm, then the desired gap distance would be 4.8 nm including two layers of binding molecules on both sides of the gap and a target chemical molecule. Note that the target molecule can occupy a size between tenths of a nanometer (gas molecules) to a few microns (airborne virus). Structure gap distances can vary depending on the desired threshold concentrations and selectivity of molecules. For example, the structure gap may be sized to accommodate a single target molecule to bridge the structure gap, although the structure gap can be sized to correspond to multiple molecule widths as well.

The example shown in FIG. 2 includes electrically conductive structures in the form of hexagonal pillars. In other examples, pillars having other cross-sectional shapes can be used. For example, pillars can be circular, square, rectangular, or triangular in shape. Although not always required, pillar structures can be arranged in a regular uniform array having constant inter-pillar gap distances across adjacent pillars throughout the structure assembly within the switch gap. However, in one alternative, the inter-pillar cap distances can be non-uniform. For example, inter-pillar gap distances can have two distances corresponding to two different target molecules, although additional gap distances and molecules can be detected, e.g. 2-10 and most often 2-4. In some examples, pillars can generally range in height from 10 nanometers to 100 micrometers. Pillars can also generally range in width from 1 nanometers to 100 micrometers.

Figure 6A:
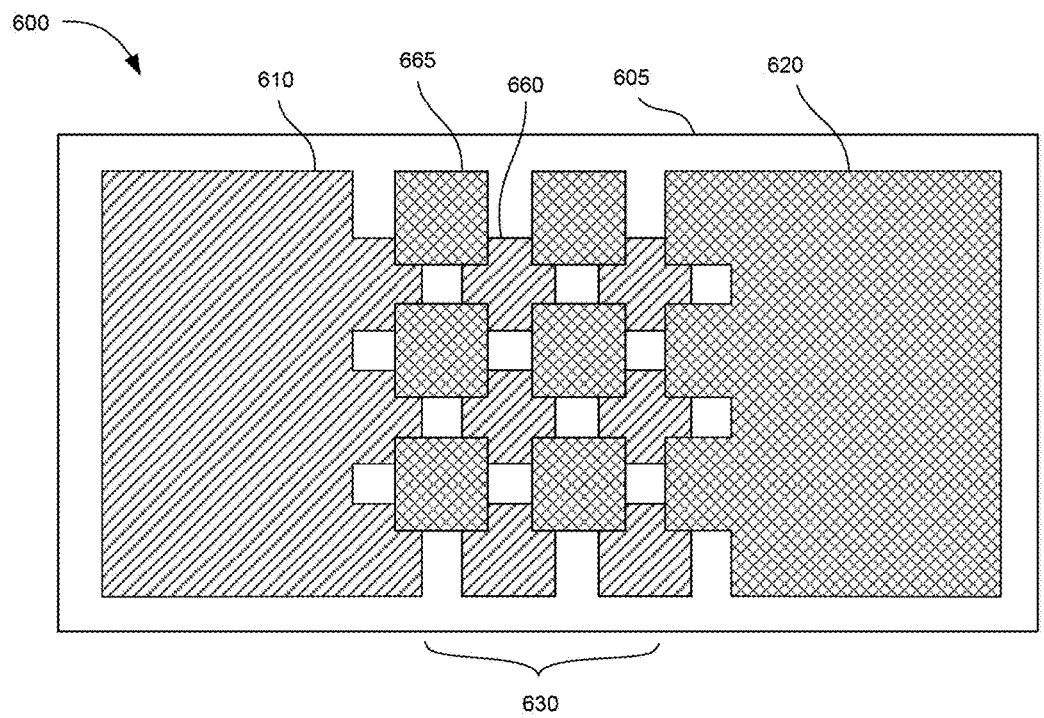
FIGS. 6A and 6B are a top view and side view, respectively, of a chemically-selective percolation switch, in accordance with examples of the present invention.
Figure 6B:
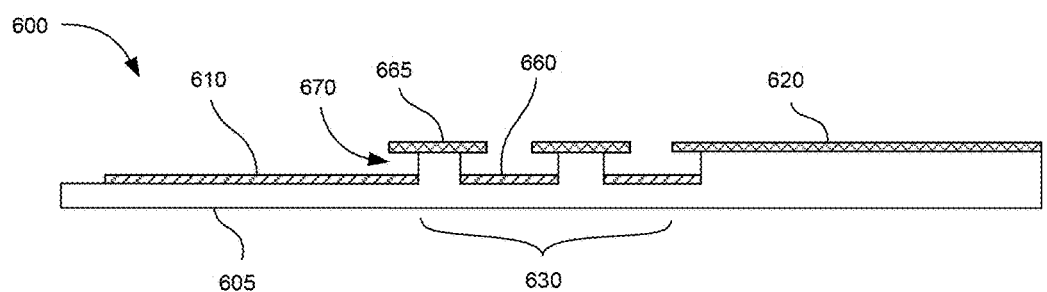

In further examples of the present invention, a chemically-selective percolation switch can include electrically conductive structures in the form of overlapping horizontal parallel plates formed in the switch gap. Thus, the structure gaps can be oriented perpendicular to the switch gaps. The parallel plates can be formed so as to create a network of fluid flow channels which allow fluid to enter and exit the switch gap and corresponding structure gaps. In one example, FIGS. 6A and 6B show a top view and side view, respectively, of such a chemically-selective percolation switch 600. The switch includes a substrate 605. The substrate can be any non-conductive material having sufficient mechanical strength to support corresponding structures and electrodes. Non-limiting examples of suitable non-conductive materials can include oxide-grown silicon, plastics, glass, and the like. In one alternative, the substrate can be flexible. On the substrate is formed a positive electrode 610 and a negative electrode 620 separated by a horizontal switch gap 630. A layer of lower horizontal plates 660 is in the same plane as the positive electrode. A layer of square-shaped upper horizontal plates 665 is parallel to the lower layer and in the same plane as the negative electrode. The lower horizontal plates vertically overlap with the upper horizontal plates at the corners of the plates. As such, the upper and lower horizontal plates can be each non-contacting one another. The lower and upper layers are separated by a vertical structure gap 670 such that the switch gap and structure gaps are perpendicular to one another. Target chemical molecules can enter the structure gaps between the plate corners to create electrically conductive pathways between the plates. When the target chemical concentration reaches the switching threshold of the switch, a sufficient number of target chemical molecules can bind between the parallel plates so that a conductive pathway forms from the positive electrode to the negative electrode.

Figure 7:
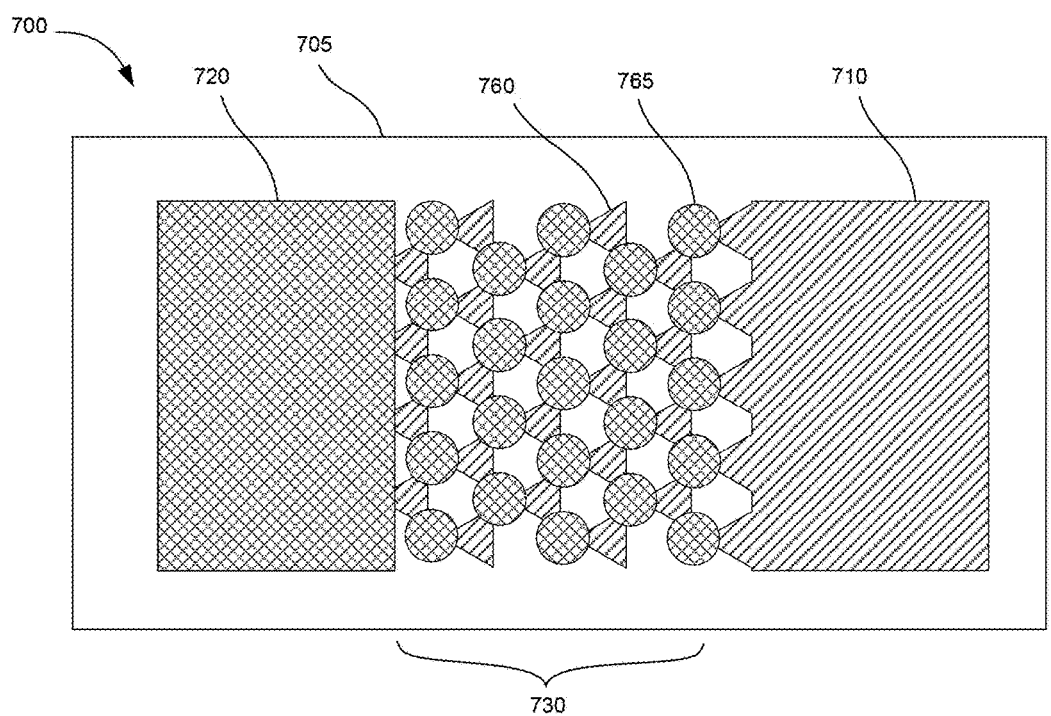
FIG. 7 is a top view of another design of a chemically-selective percolation switch, in accordance with examples of the present invention.
Figure 8A:
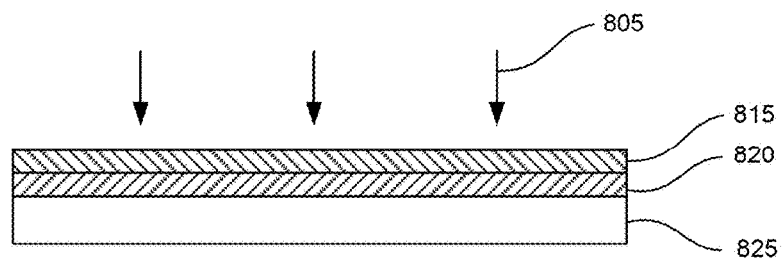
FIGS. 8A-8G show steps in a method of fabricating nano-gap structures, in accordance with examples of the present invention.
Figure 8B:
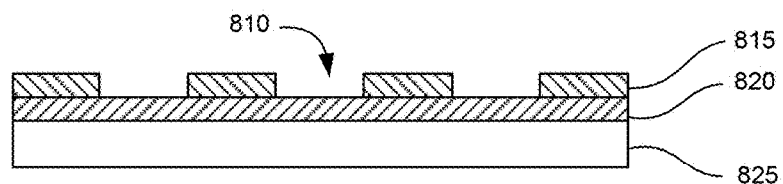
Figure 8C:
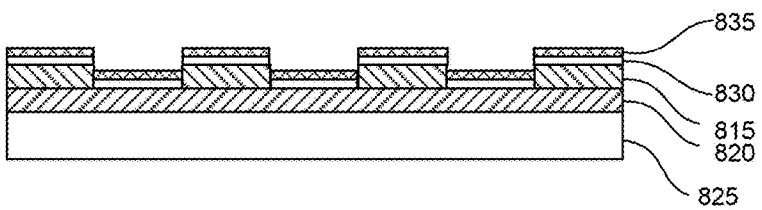
Figure 8D:
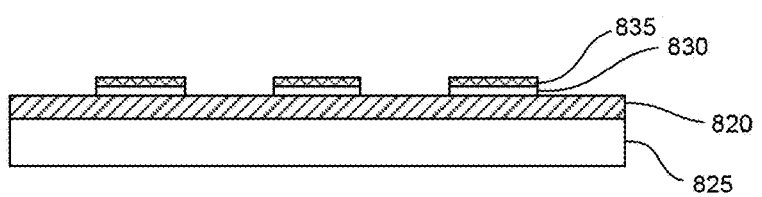
Figure 8E:
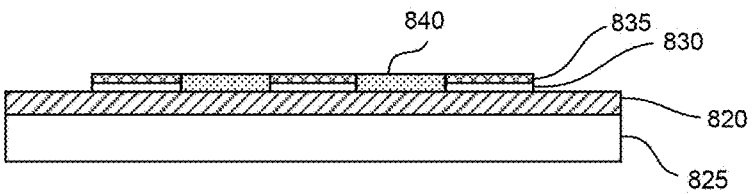
Figure 8F:
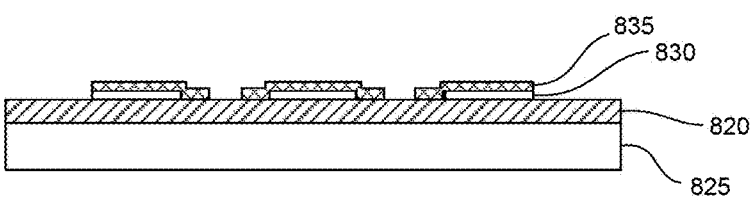
Figure 8G:
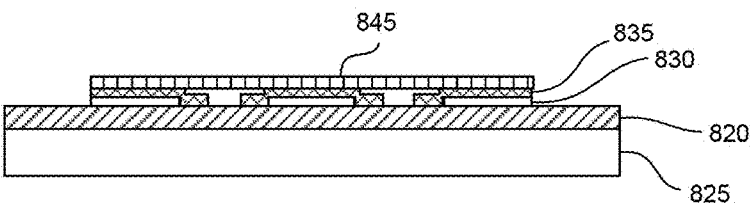

FIG. 7 shows another example of a chemically-selective percolation switch 700 which is conceptually similar to FIG. 6A while using differently shaped intermediate structures. The switch includes a substrate 705 on which is formed a positive electrode 710 and a negative electrode 720 separated by a switch gap 730. A layer of triangular-shaped lower horizontal plates 760 is in the same plane as the positive electrode. A layer of circular-shaped upper horizontal plates 765 is in the same plane as the negative electrode. The circular-shaped upper horizontal plates vertically overlap with the triangular-shaped lower horizontal plates at the corners of the triangular-shaped plates while maintaining a structure gap distance. The layers of parallel plates are separated by a structure gap. Target chemical molecules can enter the structure gaps to form a conductive pathway from the positive electrode to the negative electrode.

To reliably fabricate nano-size gaps, standard lithography with vertical pillar deposition or sacrificial layer deposition-and-removal can be utilized as a simple and robust technique, with an e-beam technique as an alternative. In one example, FIGS. 8A-8G show fabrication steps combining E-beam lithography with modified electroplating. First, an E-beam 805 is used to develop a pattern of gaps 810 on a PMMA polymer layer 815 as a sacrificial release layer. The PMMA layer is formed over a layer of $Si_xN_y/SiO_2$ 820 on a substrate of silicon 825. A layer of Cr 830 and a layer of Au 835 are deposited. The PMMA layer is then lifted off to leave metal structures formed of the Cr and Au layers as conductive structures. In some cases minimum gap distance may not reach a sufficiently small distance, such as about 10 nanometers for example, depending on limitations of the E-beam equipment. In that case, further reduction of the gap distance can be performed via a feedback-controlled electroplating method. For example, aqueous $HAuCl_4$-based electrolyte 840 can be applied between the metal structures. In order to reduce the gap distance, a voltage is applied to partially electroplate the gap. Fabrication of even sub nanometer gaps, such as 0.3-1.0 nm, is feasible using this method. Finally, a covering 845 is placed over the gaps to form nano-sized channels that can accept target chemical molecules. The covering can be formed of any suitable non-conducting material and facilitates direction of fluid flow through the nano-sized channels. Non-limiting examples of covering material can include glass, plastics, oxide-covered silicon, and the like.

FIGS. 9A-9G show another method of fabricating nano-sized gaps using vertical wall deposition, that can be accurately formed via high-precision atomic layer deposition (ALD). Ultraviolet radiation 905 directed through a mask 910 is used to pattern a layer of $SiO_2$ 915 and a layer of polycrystalline silicon 920. The polycrystalline silicon layer is formed over a layer of $Si_xN_y$ 925 over a substrate of silicon 930. $SiO_2$ is then deposited on interior surfaces of the gaps through plasma-enhanced chemical vapor deposition (PECVD) (FIG. 9C). Then the $SiO_2$ is etched from the surface and the bottom surfaces of the gaps by inductively coupled plasma (ICP) etching (FIG. 9D). The polycrystalline silicon is etched away with KOH to leave vertical walls of $SiO_2$ (FIG. 9E). An Au layer 935 is deposited between the vertical walls by atomic layer deposition (FIG. 9F). The vertical walls can then be etched away with BHF to leave nano-sized gaps between Au structures. Clearly, alternative materials can be used for each of the layers as long as the above outlined process and results can be achieved. For example, conductive materials other than Au can be used such as, but not limited to, Cu, Ag, conductive polymers, metals, and the like. Similarly, sacrificial spacing materials other than $SiO_2$ can also be suitable, while other known insulating and semi-conducting materials can also be used.

In some examples, the chemically-selective percolation switch sensors can be fabricated by a combined microfabrication and chemistry procedure. In one example, a fabrication method can include precisely defining a switch gap in the range of 10 nm~50 μm. Due to lithographic limitations, a 10 nm gap can be defined by the e-beam nanolithography or the thickness of a deposited layer.

Figure 10A:
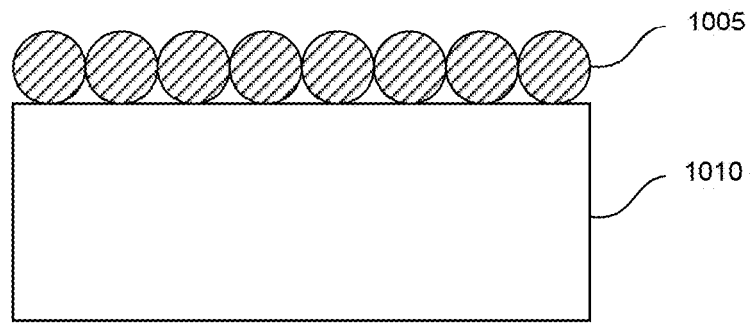
FIGS. 10A-10C show steps in a method of forming nano-sized vertical pillars, in accordance with examples of the present invention.
Figure 10B:
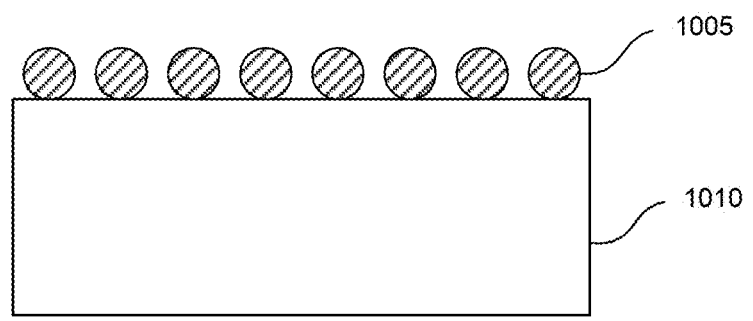
Figure 10C:
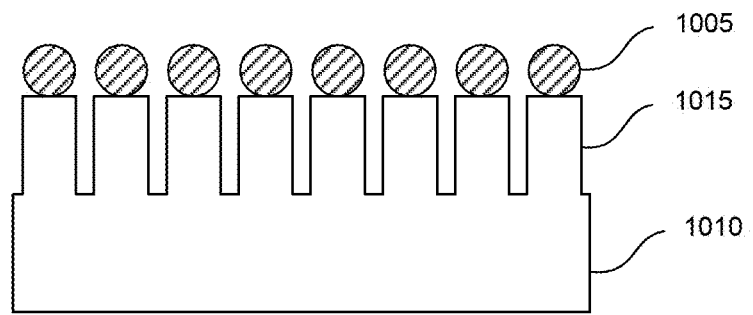

As mentioned above, in some examples the chemically-selective percolation switch can include vertical pillars within the switch gap. FIGS. 10A-10C show one example of a method of forming nano-size vertical pillars. First, polystyrene beads 1005 are spin-coated onto a substrate 1010 (FIG. 10A). The bead size is reduced by plasma etching (FIG. 10B). Then, the exposed substrate is etched by deep reactive-ion etching (DRIE) to form nano-sized pillars 1015 (FIG. 10C). In some examples, the substrate can be silicon. After forming nano-sized pillars, the pillars can be plated with a conductive material such as gold to for electrically conductive pillars. Additional details on pillar formation techniques can be found in Cheung et al, *Fabrication of nanopillars by nanosphere lithography*, Nanotechnology, 1339-1343 (2006). Similar vertical pillars can be formed by any suitable technique.

Figure 11A:
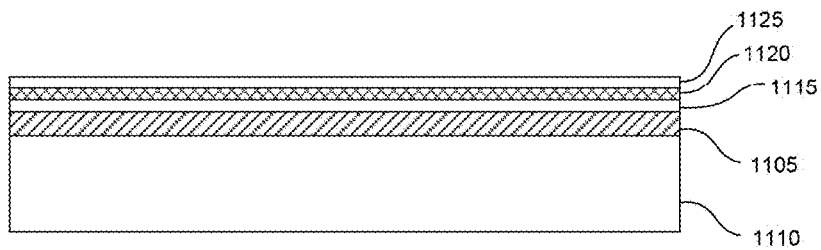
FIGS. 11A-11D show steps in a method of fabricating nano-gap structures, in accordance with examples of the present invention.
Figure 11B:
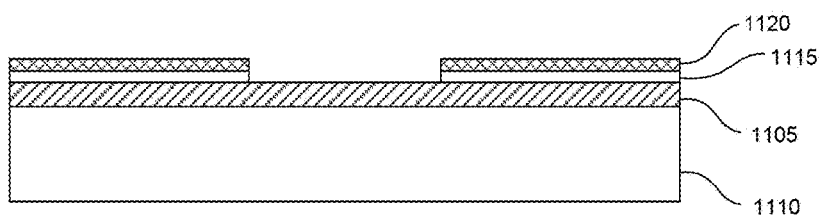
Figure 11C:
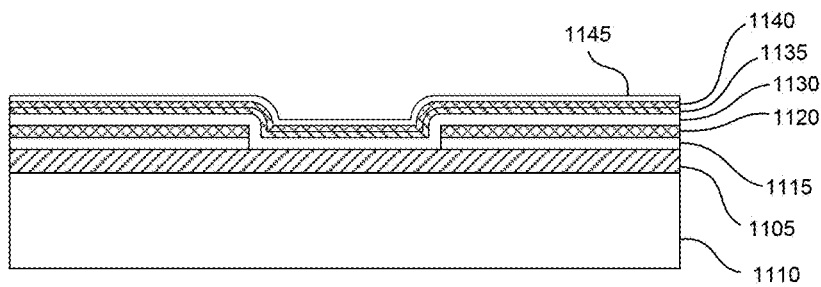
Figure 11D:
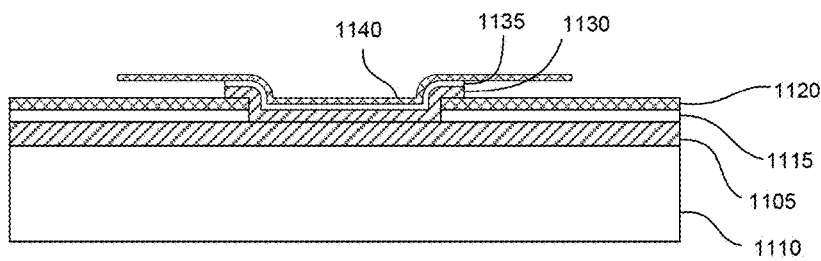

FIGS. 11A-11D illustrate a method of making a nano-gap device in accordance with yet another example where substrate gaps are oriented vertically perpendicular to a switch gap. This nano-gap device uses parallel horizontal plates as the conductive intermediate structures in the switch gap. FIG. 11A illustrates $SiO_2$ 1105 deposited on a substrate 1110, followed by a 20 nm Cr layer 1115, a 200 nm Au layer 1120, and a 10 nm Cr layer 1125. The Cr layer acts as a mask. FIG. 11B illustrates a first layer patterning step where Cr and Au are etched according to a pattern. Resist is stripped and Cr-mask is etched away. In FIG. 11C a second layer set is deposited. Specifically, a 4 nm $Al_2O_3$ layer 1130 and 2 nm adhesion Si layer 1135 are deposited. A 200 nm Au layer 1140 and Cr-mask layer 1145 are also deposited. FIG. 11D illustrates a second patterning step where Cr and Au are etched, resist is stripped, and Si and Cr are also etched to form a nanogap device. Materials and layer thicknesses can be varied to achieve a desired configuration and taking into account typical semiconductor fabrication considerations (e.g. costs, equipment, performance, etc).

Figure 12A:
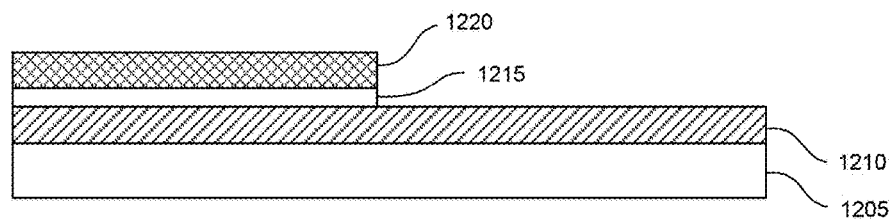
FIGS. 12A-12D show steps in a method of fabricating nano-gap structures, in accordance with examples of the present invention.
Figure 12B:
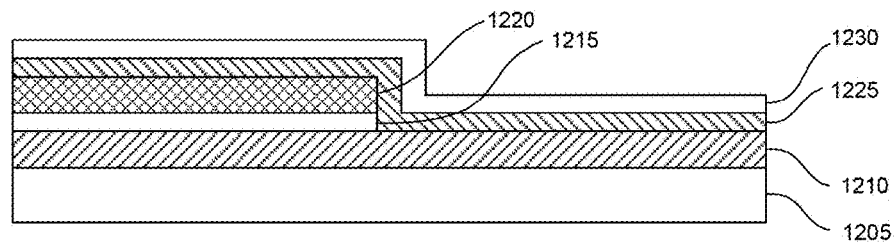
Figure 12C:
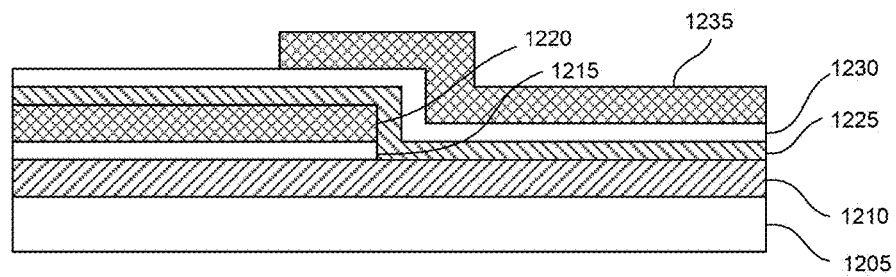
Figure 12D:
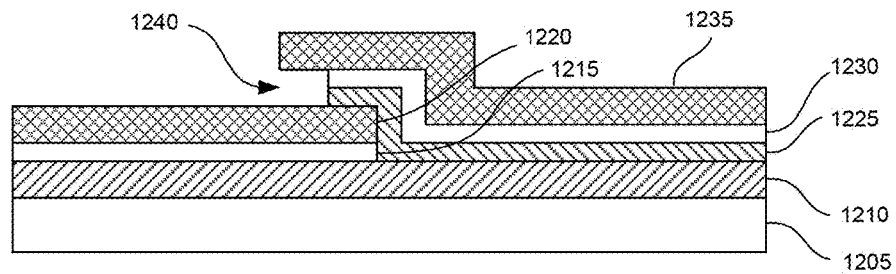

FIGS. 12A-12E illustrate yet another example of a method of manufacturing nanogap devices. FIG. 12A shows a silicon substrate 1205 with a $SiO_2$ layer 1210, Cr layer 1215, and Au layer 1220 deposited thereon. In FIG. 12B, a $Al_2O_3$ layer 1225 a $TiO_2$ layer 1230 are deposited. In FIG. 12C, a second Au layer 1235 is added. In FIG. 12D, a portion of the $Al_2O_3$ and $TiO_2$ layers are removed to leave a structure gap 1240 between the Au layers. Sacrificial layer can be $Al_2O_3$ and Si, $Al_2O_3$ and $TiO_2$, or the like. In another example, a silicon layer can be used in place of the $TiO_2$ layer.

The chemically-selective percolation switches according to the present invention can be designed to have any of a wide range of threshold target chemical concentrations, depending on the desired sensing threshold. In some examples, the threshold concentration can depend in part on residence time of target chemical molecules or particles in the binding sites of the switch. In certain examples, particle residence time in a binding site can be from 10 milliseconds to 100 seconds. Notably both threshold concentrations and adsorption period (switch-on-period) can be designed by selecting gap distance, binder types and densities, which enables programmability of detection levels.

In further examples, particle adsorption to the binding sites can be specific through ultra-selective host-guest recognition. This host-guest recognition is the process of holding molecules without covalent (permanent) bonding. A target molecule is adsorbed by a host molecule, such as a crown ether, only when the size, shape and charge-distribution of the target and the host match with each other, leading to ultra-specific binding. Since this does not form covalent bonding, the binding can be breakable, and the host thermodynamically desorbs the target molecules to reach a lower Gibbs energy equilibrium, enabling reversibility of adsorption. The reversibility depends on adsorption process (instead of absorption) where particles only temporarily attach onto the binding sites. As the adsorption period becomes longer, then the reversibility time becomes longer. The length, charges, etc. of the chemical tether can be selected to tune the half-adsorption-lifetime of the receptor complex. Note that the reversibility of the chemically-selective percolation switch is related to the 'group' reversibility or the percolation period based on these individual adsorption periods, upon the removal of target concentrations.

Figure 13:
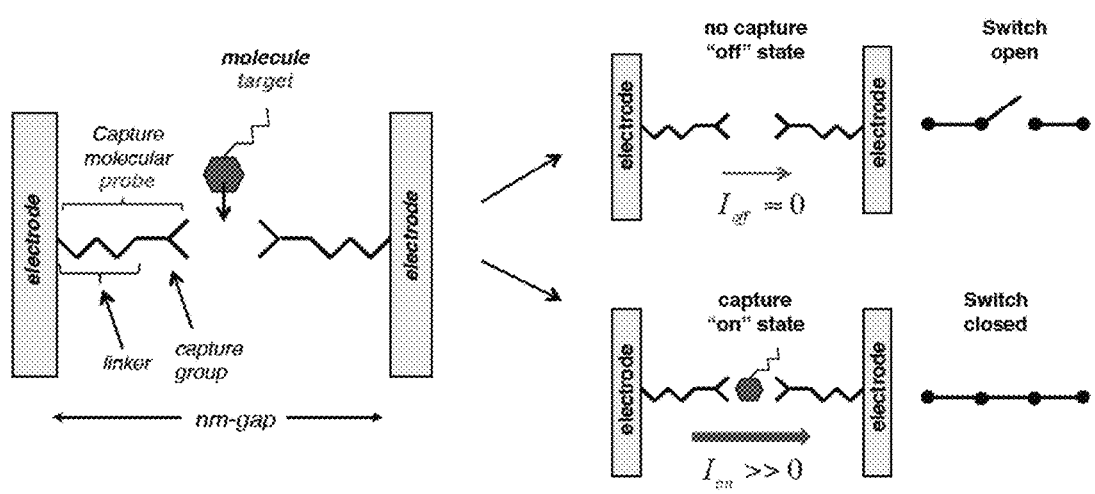
FIG. 13 shows a representation of a target molecule being captured between host molecules on electrodes, in accordance with examples of the present invention.

FIG. 13 shows a conceptual representation of a nano-gap between two electrodes with host molecule, also referred to herein as a binding agent, a binder, or a capture molecule, attached to each electrode. In this example, the gap distance is designed to be sufficient to accommodate the host molecules on either side of the gap and a single target molecule that can become bound between two host molecules. When the target molecule is captured by the host molecules, a pathway for electron tunneling is formed between the electrodes and the electric current between the electrodes is much larger than the electric current without a bound target molecule. In some examples, the host molecule can include a linker group with a capture group at the end, as shown in FIG. 13. Although a wide variety of capture groups can be suitable depending on the particular target molecule, non-limiting examples of capture groups can include PEG, cavadarine, and the like.

The chemically-selective percolation switches as described herein can be designed to detect a variety of target chemicals. In certain examples, the target chemicals can be chemical warfare agents, including paralytic shellfish toxins (PST), such as saxitoxin, tetrodotoxin, zetekitoxin, chiriquitoxin, or sarin. In other examples, the target chemical compound can be a fuel, an air pollutant, an airborne compound, an explosive, an airborne biological agent, or combinations thereof. Ultra-selectivity for these target chemicals, without the assistance of electronic pattern recognition, can be achieved by synthesizing and employing sophisticated chemistry binding that adsorbs only particular targets. Thus, bonding with the target molecule can be via hydrogen bonding, covalent bonding, van der Waals attraction, or any other association which allows electron transfer through the target molecule.

In one specific example, a chemically-selective percolation switch can include nano-gaps treated with amine-PEG-amine and crown-tetracarboxylic-acid layers, forming binding sites for target molecules. The configuration of the chemically-selective percolation switch can include electrically conductive structures with an interdigitated shape to accommodate multiple gaps in series.

In some examples, the threshold concentration of a switch can be adjusted by adjusting the surface concentration of binding agent linked to the surfaces of electrodes and/or electrically conductive structures in the switch. For example, a higher surface concentration of binding agent can make it more likely for bridges to form between the electrodes, thus reducing the threshold concentration of target chemical required to close the switch. Similarly, a lower surface concentration of binding agent can result in a higher threshold concentration for the switch. Surface concentration can be controlled by treating the electrodes with a solution having a known concentration of the binding agent. In some cases, a treatment solution can include a binding agent that is active for binding the target chemical as well as a non-binding agent that can link to the electrode surfaces, but which will not bind the target chemical. The proportion of the binding agent and non-binding agent can be adjusted to control the surface concentration of the binding agent on the electrodes. In one example, the binding agent and non-binding agent can link to the electrode surfaces through a linking group such as a thiol group, an amine group, a siloxy group, and others.

In a certain example, the binding agent can be applied to the electrodes using a compound comprising two binding agent groups attached to a central photocleavable group. This compound can be applied to electrodes with a nano-gap with a gap distance that is approximately the same as the length of the compound. After the binding agent groups link to the electrode surfaces on each side of the gap, the photocleavable group can be removed to leave two binding agents attached to the electrodes on opposite sides of the gap. This can ensure that the binding agents are aligned so that a target chemical molecule can be captured between the binding agents.

The selection of binding agents can also affect the threshold concentration of the chemically-selective percolation switch. Binding agents can be selected to have a high degree of conjugation to allow for more electrical conductivity. The length of the binding agent molecules can also be selected to make an appropriately sized space for a single target chemical molecule to be capture between two binding agent molecules. The type of capture group on the binding agent molecule can be selected to match with the target chemical. For example, the capture group can include hydrogen bond donors spaced apart at a distance that matches with hydrogen bond acceptors on the target molecule. Conversely, if the target chemical has hydrogen bond donors then the capture group on the binding agent can have matching hydrogen bond acceptors. In one particular example, saxitoxin can be the target chemical. Saxitoxin has 2 hydrogen bond donors spaces about 7 angstroms apart. Therefore, an effective capture group for saxitoxin can include 2 hydrogen bond acceptors spaced 7 angstroms apart. In another example, sarin has 2 hydrogen bond acceptors spaced about 3 angstroms apart. Therefore, an effective capture group for sarin can have 2 hydrogen bond donors spaced 3 angstroms apart.

The strength of interaction between the target chemical and the binding agent can affect the on-rate and off-rate of target chemical molecules bound to the binding agent. The off-rate can also be affected by the geometry of the switch. For example, a switch can include vertical pillars in the switch gap. The vertical pillars can be treated with a binding agent. The structure gap distance between the pillars can be sufficient to allow a single molecule of the target chemical to be bound between binding agent molecules attached to opposite pillars. In this example, the height of the pillars is one parameter that can be adjusted to change the off rate of the target chemical molecules bound in the structure gaps between the pillars. When the pillars are taller, a target chemical molecule can have a longer distance over which to diffuse in order to exit the structure gap between the pillars.

While the target chemical molecule is moving through the structure, the target chemical molecule can become bound to other binding agent molecules. Thus, a target chemical molecule can take a longer time to become completely unbound from the binding agent molecules on the pillars. A slower off-rate can result in a lower threshold concentration for the switch because bound target chemical molecules tend to maintain an electrically conductive bridge for a longer period of time.

Figure 14:
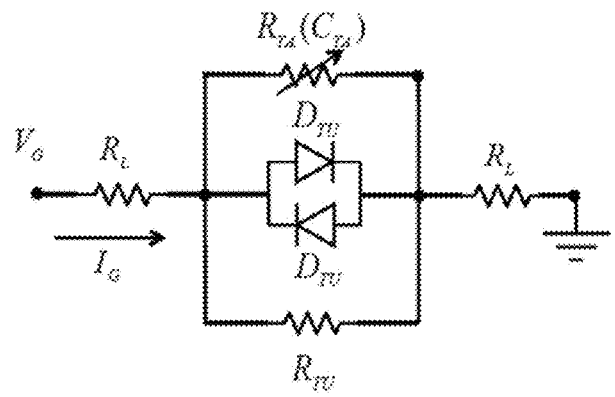
FIG. 14 shows a circuit model of a junction between electrodes treated with a binding agent in the presence of a target chemical, in accordance with examples of the present invention.
Figure 15:
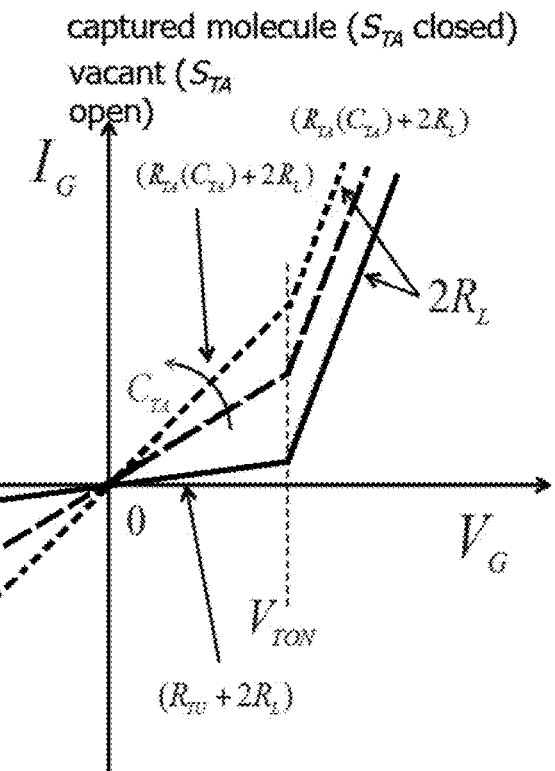
FIG. 15 is an IV graph illustrating binding response of the circuit model of FIG. 14.
Figure 16:
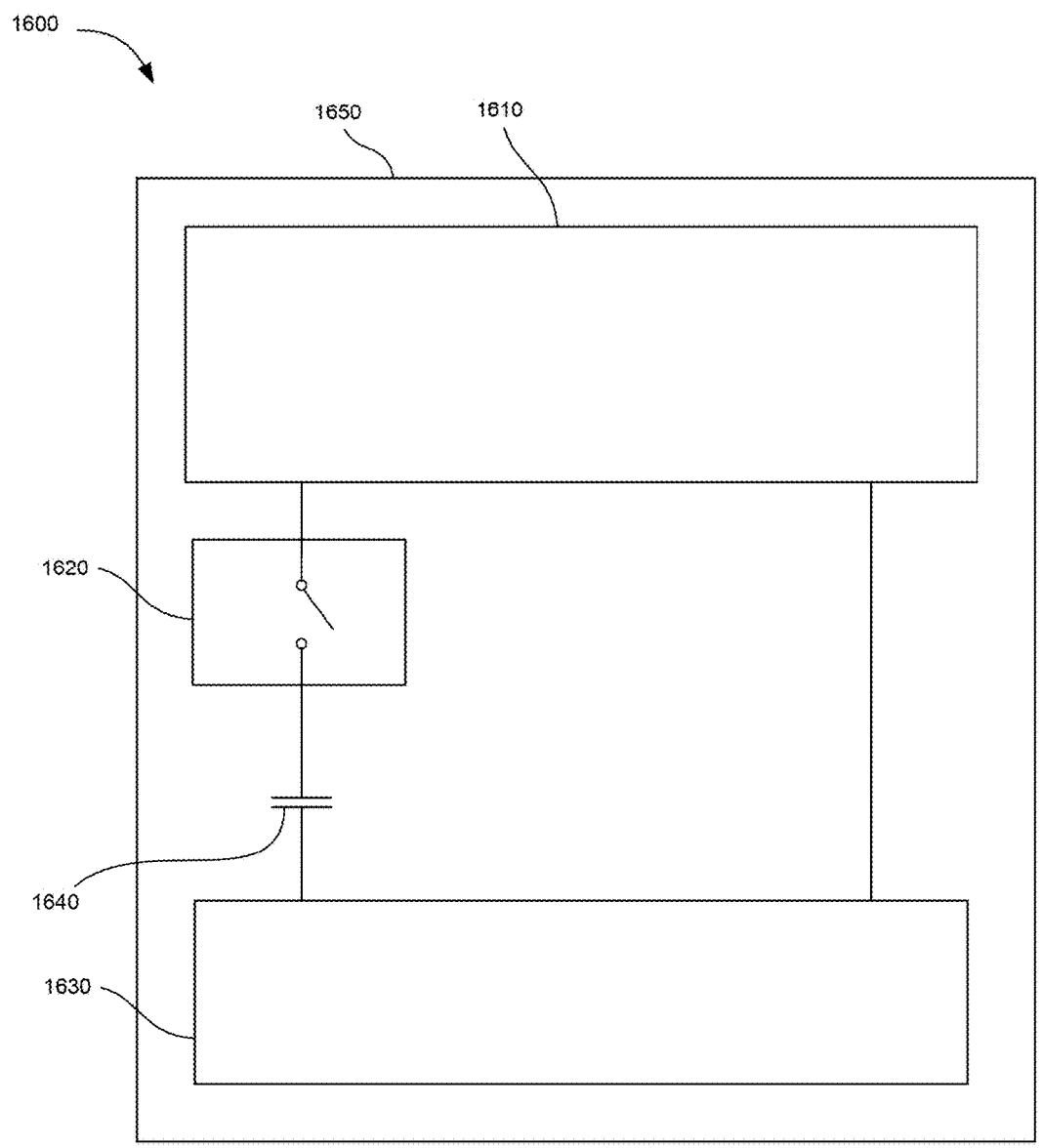
FIG. 16 is a schematic of a zero-power digital chemical analyzer, in accordance with examples of the present invention.
Figure 17:
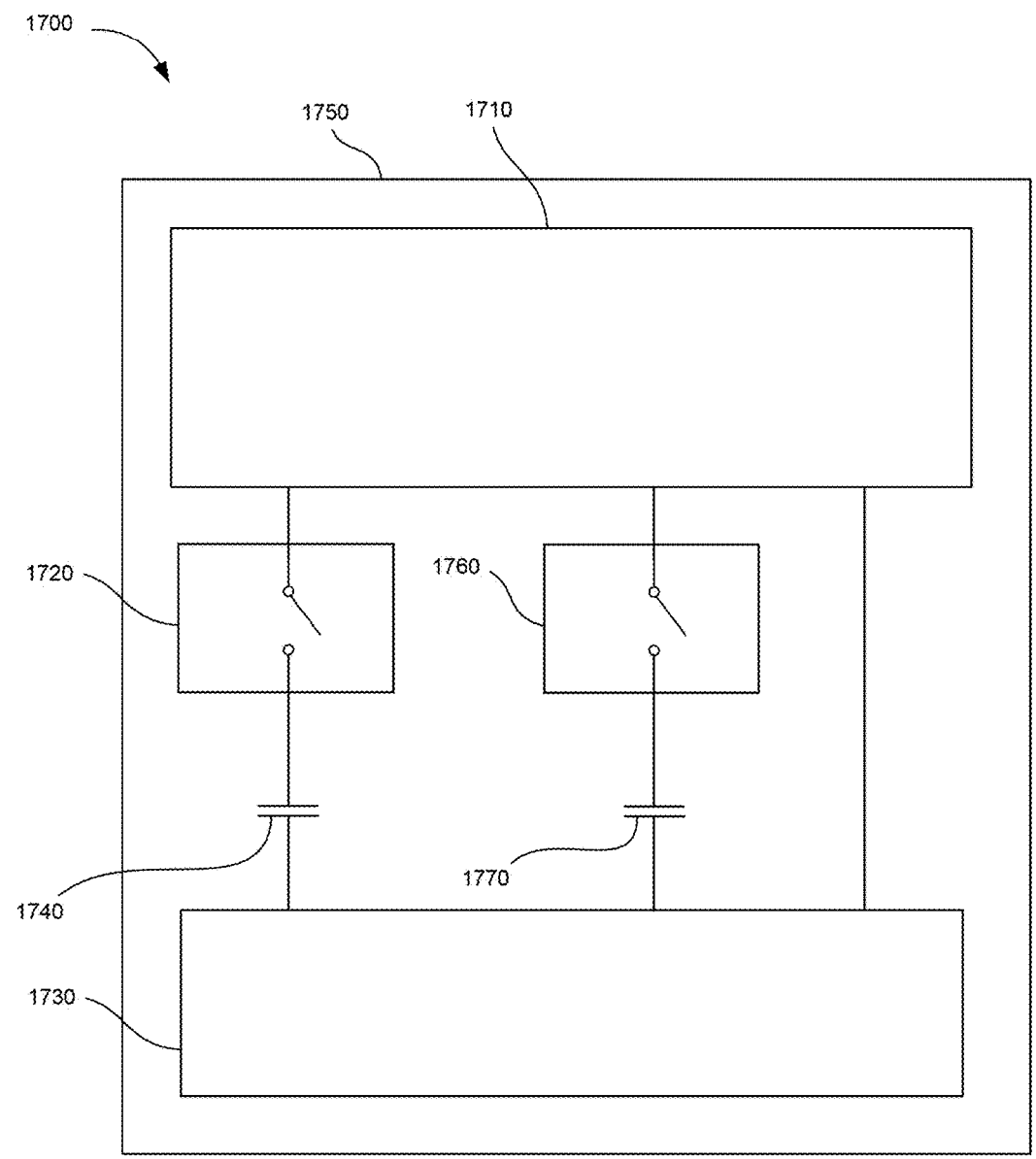
FIG. 17 is a schematic of a digital chemical analyzer with two switches in parallel as an example, in accordance with examples of the present invention.

FIGS. 14-15 shows a model of the junction between two electrodes treated with a binding agent in the presence of a concentration $C_{TA}$ of a target chemical. The junction is modeled with the circuit diagram shown in FIG. 14, and the qualitative behavior of the voltage $V_G$ vs. current $I_G$ is also graphed in FIG. 15. In FIG. 14-15, $R_L$ is the resistance of the binding agent molecules, $R_{TU}$ is the resistance of tunneling across the gap unoccupied by a target chemical molecule, $R_{TA}(C_{TA})$ is the resistance across bound target chemical molecules (which is dependent on the concentration of the target chemical), and $D_{TU}$ represents field dependent tunneling. $R_{TA}$ is assumed to be much less than $R_{TU}$ and $R_L$ is assumed to be less than $R_{TA}$. The behavior of this circuit is shown in the graph of FIG. 15, with the solid line representing an open switch without a bound target chemical and the dotted line representing a close switch with a high concentration of bound target chemical. The dashed line between these two represents an intermediate concentration of target chemical.

The critical or threshold concentration of the target chemical can also be modeled mathematically using the following equations:

$$C_{JS} = \lambda \cdot C_{PS}^2 \cdot C_{TS} \quad (1)$$

$$C_{TS} = a \cdot C_{TA} \quad (2)$$

$$N_J = A_{el} \cdot C_{JS} = A_{el} \cdot \lambda \cdot a \cdot C_{PS}^2 \cdot C_{TA} \quad (3)$$

$$1 = A_{el} \cdot \lambda \cdot a \cdot C_{PS}^2 \cdot C_{TAC} \quad (4)$$

$$C_{TAC} = \frac{1}{A_{el} \cdot \lambda \cdot a \cdot C_{PS}^2} \quad (5)$$

In Equations 1-5, $C_{JS}$ is the surface concentration of junctions made up of a target molecule bound between two binding agent molecules; $\lambda$ is a constant that can be determined experimentally; $C_{PS}$ is the surface concentration of binding agents (i.e., probes); $C_{TS}$ is the surface concentration of target molecules; $\alpha$ is the volume-to-surface conversion coefficient; $C_{TA}$ is the volumetric concentration of target molecules present; $N_J$ is the number of junctions; $A_{el}$ is the surface area of the electrode; and $C_{TAC}$ is the critical or threshold concentration of target chemical for the switch to close (N=1 in this case because a single junction can form a bridge between the electrodes). Thus, the threshold concentration is inversely proportional to the area of the electrode and the surface concentration of binding agent on the electrode surface.

In certain examples, the threshold concentration can be adjusted within a wide range, e.g. from 1 part per billion (ppb) to 100 part per million (ppm), and in some cases to 1000 ppm, depending on the switch geometry, binding agents and target molecules.

The chemically-selective percolation switches described herein can be used in zero-power digital chemical analyzers. In some examples, a zero-power digital chemical analyzer can include a power supply, a detection circuit, and a chemically-selective percolation switch electrically connected between the power supply and the detection circuit. The chemically-selective percolation switch can be configured to switch the detection circuit to an on state when the switch is exposed to a threshold concentration of a target chemical compound.

In certain examples, the chemically-selective percolation switch can conduct a trivial current of less than 1 pA (and in some cases less than 1000 pA at 1V) when the chemically-selective percolation switch is exposed to a concentration of the target chemical compound below the threshold concentration. The switch can conduct a significant amount of current of at least 1 nA when the chemically-selective percolation switch is exposed to the threshold concentration of the target chemical compound, forming an electrically-conductive path via the natural percolation phenomenon.

In some examples of the present technology, a zero-power digital chemical analyzer can be used to identify the presence of specific aerosol and vapor-phase chemical signatures, thus producing a digital output code identifying the target species when the concentration of the target species exceed as specified threshold. The zero-power chemical analyzer can include one or more chemically-selective percolation switches, which dramatically change resistance when exposed to a specific compound. None of these mechanisms require external power consumption other than for the provision of bias and the switching output voltage, and yet the system has the potential to digitally sense vapor concentrations in the ppm and ppb range, depending on the particular materials. This system can be used to detect many different chemical targets, several non-limiting examples of which include chemical-warfare-agent (CWA) aerosols and vapors, fuel, and explosive vapors.

In order to meet the 'zero-power' requirements while maintaining selectivity, sensitivity, and digitization capability of target chemical inputs, the system can take advantage of the mechanism of percolation of the target chemical species. Specifically, the chemically-selective percolation switches can use a chemically-selective percolation phenomenon to control the electrical conductivity between two electrodes. Random motions of particles can cause the particles to adsorb onto a binder-filled surface and form a particle bridge across a gap, if the concentration of the particles exceeds a certain threshold. Due to the particle bridge, a conductive path can be formed between the two electrodes for a limited adsorption period, transferring the electric potential from the input (battery) to the output and electrons conduct through the gap via percolated particles. When the concentration of target gas compounds is below the threshold, the gap remains open without a conduction path, enabling nearly 'zero'-power operation. Notably both threshold concentrations and adsorption period (switch-on-period) can be designed by selecting gap distance, binder types and densities, which enables programmability of detection levels. The binders can be chemically-designed through ultra-selective host-guest recognition between the binder and the chemical target.

The chemically-selective percolation switches can be used both as a sensing mechanism for detecting a certain level of the chemical target, and also as an electrical switch for activating the zero-power digital chemical analyzer from a zero-power "off state" to an "on state" when electrical current flows through the chemically-selective percolation switch. According to the chemically-selective percolation mechanism, when aerosol particles of the chemical target selectively adsorb onto a binder-filled surface the particles can form a particle bridge across a gap if their concentrations exceed a critical concentration or percolation threshold. The resulting particle bridge can establish an electrically conductive path between two electrodes spaced by a narrow gap transferring the electric potential from the input (battery) to the output. Since electrons jump through the gap via tunneling, the electrical current increases exponentially due to the reduced effective gap distance. The switching device is in the 'off-state' when the gap is e.g. >10 nm, blocking current flows and resulting in off-current near zero (e.g. <1 pA), enabling near 'zero'-power operation. In the 'on' state the electrical current through the particle path is sufficient, e.g. in the nA~μA range. The percolation sensor is also reversible as the adsorbed particles can also desorb.

Preventing false signals is another aspect of realizing a distributed zero-power sensor network. False signals are triggered by either rare statistical distribution of target binding or random landing of non-specific molecules over the gap between the two electrodes, respectively, forming a conductive bridge for unwanted current flow. Both the false alarm and detection probabilities, caused by rare statistical distribution, can be computed by integrating the areas under the percolation curve (FIG. 5) in relation to a threshold and then comparing it to the ideal probability. The results show that if a threshold concentration is set as 0.5, the CPS would result in a false alarm rate of 2.10% and a detection probability of 96.07%. To prevent false signals from random landing, a configuration of multiple gaps (e.g. structure gaps) along one conductive path or a preventive array of posts can be adopted as described previously with respect to structure-assisted percolation. While the probability of capturing target molecules at each gap is identical, that of random particles landing at each gap is not causal, thus resulting in significant suppression of false conduction. In some examples, a 2-gap configuration can suppress the false rate to <0.01% at slight sacrifice of detection probability, if needed. The temperature dependence of the percolation-based resistance in the discontinuous film was given by: $R \propto e^{\beta L} e^{E_c/k_B T}$ where L is the mean size of the gap between clusters, $\beta = \sqrt{8mU_0/(h/2\pi)^2}$ (with m the effective mass of an electron and $U_0$ the height of the barrier), $E_c$ is the Coulomb charging energy of a metallic island, $k_B$ the Boltzman constant and T the temperature in K. Based on the equation the temperature variation of the CPS outputs is estimated as by 5.1% as the temperature increases from −60° C. to 120° C. (military standard range) excluding the degradation of binding sites. Humidity dependence has been reported as less significant in literature. The sensitivity of the CPS sensor is the slope of the output current vs. target concentration, and its values vary depending on both geometry (electrode width, length) and materials (binding site densities). The higher sensitivity can be obtained at a shorter gap distance and a longer adsorption period. In some examples, the sensitivity of 74 dB in nA-decade/ppm-decade when the chemically-selective percolation switch utilizes an electrode of 100×100 nm² footprint with an adsorption period of 30 sec. The corresponding detectable concentration is estimated to be $10^{21}/m^3$ or a sensitivity of 1.0 ppm. The subthreshold-swing was computed as 12.5 dB/dec, which can be further improved by controlling design parameters mentioned above.

Considering on-current of 1 nA, the chemically-selective percolation switch can require 1 ms to produce output voltage of 1 V by charging an output capacitor of 1 pF. Considering the saxitoxin molecular diameter of 3 nm and adsorption time of 30 ms, current percolation simulation model indicates that a chemically-selective percolation switch with an inter-electrode area of 1×1 $\mu m^2$ would require 300 ms for a saxitoxin density of $10^{21}/m^3$ (corresponding to 1.0 ppm) to percolate and form a conductive path. Decreasing the area to 100×100 $nm^2$ would increase the percolation probability and decrease the detection time by ~10 folds. By increasing the adsorption time from 30 ms to 300 ms, the simulation results predicted a decreased threshold value of 74 ppb. In one example, the detection sensitivity can reach to the lethal dose of 3.0 ppb by reducing the electrode gap to 10×10 $nm^2$ and increasing the adsorption time up to 10 s.

FIG. 16 shows an example of a zero-power digital chemical analyzer 1600. A power supply 1610 such as a battery is connected in a circuit with a chemically-selective percolation switch 1620 and detection circuitry 1630. A capacitor 1640 can be connected between the chemically-selective percolation switch and the detection circuitry such that the capacitor 1640 charges until voltage is detectable. As charging continues, the voltage at the capacitor increases to reach a certain electrical voltage that is sufficiently high enough to turn on the rest of the electronics powered by the attached battery or power supply. In this example, each of the circuit elements can be placed on a substrate 1650 such as a circuit board. When the chemically-selective percolation switch is exposed to a threshold concentration of a target chemical compound, the switch can "close" to complete the circuit and allow electric current to flow to the detection circuitry.

The present invention also extends to digital chemical analyzers that can include multiple chemically-sensitive percolation sensors that are tuned to different threshold concentrations. The analyzer can determine the ambient concentration of the target chemical based on the switching threshold concentrations of the switches that are closed. FIG. 17 shows an example of a digital chemical analyzer 1700. As in the digital chemical analyzer shown in FIG. 16, this digital chemical analyzer includes a power supply 1710 connected in a circuit with a chemically-selective percolation switch 1720 and detection circuitry 1730. A capacitor 1740 can be connected between the chemically-selective percolation switch and the detection circuitry. Each of the circuit elements can be placed on a substrate 1750 such as a circuit board. This example also includes a second chemically-selective percolation switch 1760 and a second capacitor 1770. The chemically-selective percolation switches can be tuned to have different threshold concentrations so as to allow extrapolation of target molecule concentrations with more precision. In further examples, more chemically-selective percolation switches can be added to increase the detection resolution of the digital chemical analyzer.

In further examples, a digital chemical analyzer can include multiple chemically-selective percolation switches that are configured to detect different target chemical compounds. For example, a single analyzer can detect zetekitoxin, tetrodotoxin and chiriquitoxin by incorporating parallel switches that are configured to selectively detect these target compounds.

In one example, a zero-power digital chemical analyzer can include a power supply, a detection circuit, a first chemically selective percolation switch electrically connected between the power supply and the detection circuit, wherein the chemically-selective percolation switch is configured to switch the detection circuit to an on state when the chemically-selective percolation switch is exposed to a threshold concentration of a target chemical compound, and a second chemically-selective percolation switch connected in series with the chemically-selective percolation switch so that the detection circuit is not switched to the on state unless both the chemically-selective percolation switch and the second chemically-selective percolation switch conduct electric current from the power supply, wherein the second chemically-selective percolation switch is tuned to conduct electricity via the natural percolation phenomenon when exposed to the same threshold concentration of the target chemical compound as the chemically-selective percolation switch.

In another example, a digital chemical analyzer can include a power supply, a first chemically-selective percolation switch tuned to conduct electric current from the power supply when exposed to a first threshold concentration of a target chemical compound, and a second chemically-selective percolation switch tuned to conduct electric current when exposed to a second threshold concentration of the target chemical compound, wherein the second threshold concentration is greater than the first threshold concentration. In a further example, the digital chemical analyzer can include a detection circuit electrically connected to the first and second chemically-selective percolation switches, wherein the detection circuit is configured to determine a minimum ambient concentration of the target chemical compound based on signals from the first and second chemically-selective percolation switches.

EXAMPLES

Figure 18:
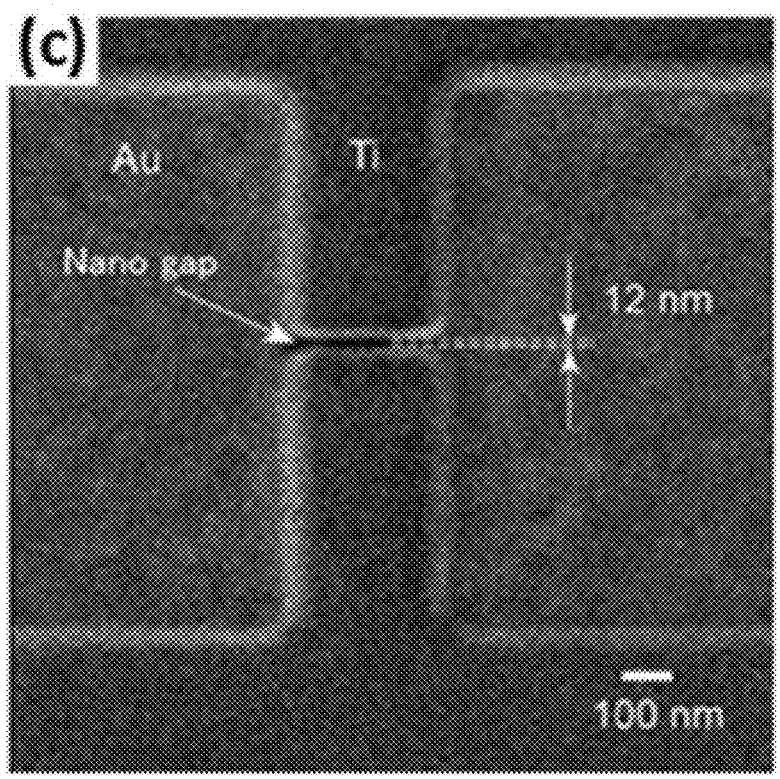
FIG. 18 is an SEM image of a nano-gap between gold electrodes, in accordance with examples of the present invention.

FIG. 18 is an SEM image of a nano-gap between gold electrodes. The switch gap distance was 12 nanometers. This nano-gap was formed by focused ion beam patterning.

Figure 19:
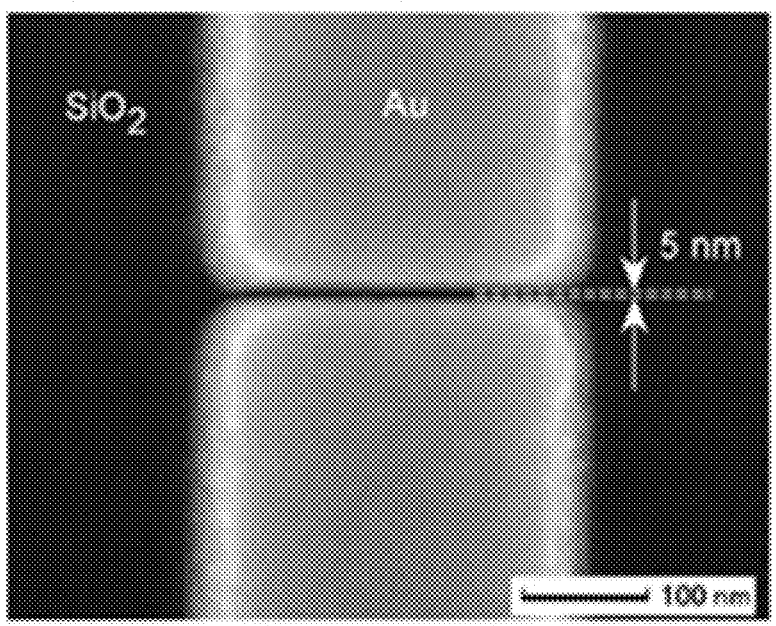
FIG. 19 is an SEM image of a nano-gap between electrodes, in accordance with examples of the present invention.

FIG. 19 is an SEM image of another nano-gap formed using focused ion beam patterning. This nano-gap had a gap distance of 5 nanometers.

Figure 20A:
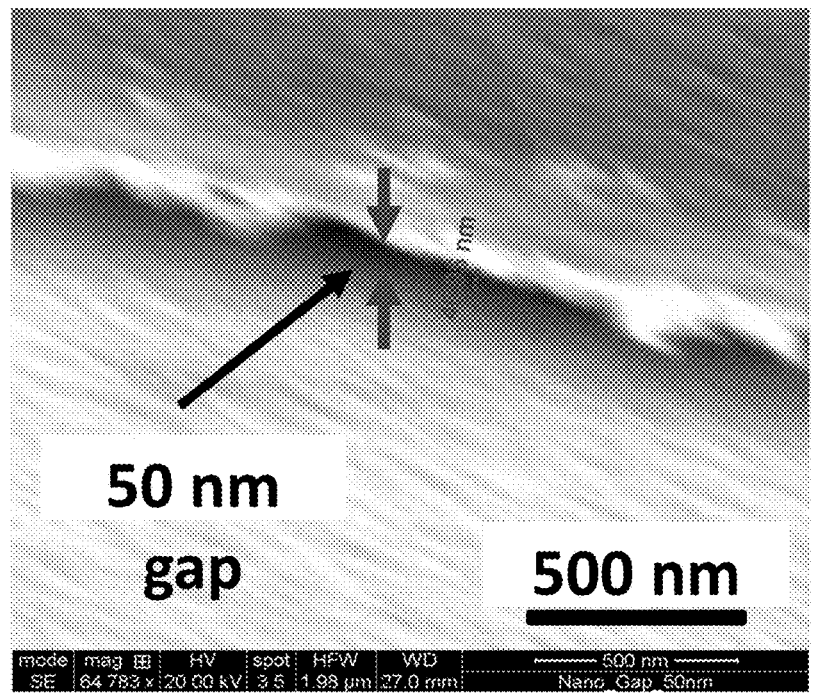
FIG. 20A is an SEM image of a nano-gap between electrodes, in accordance with examples of the present invention.
Figure 20B:
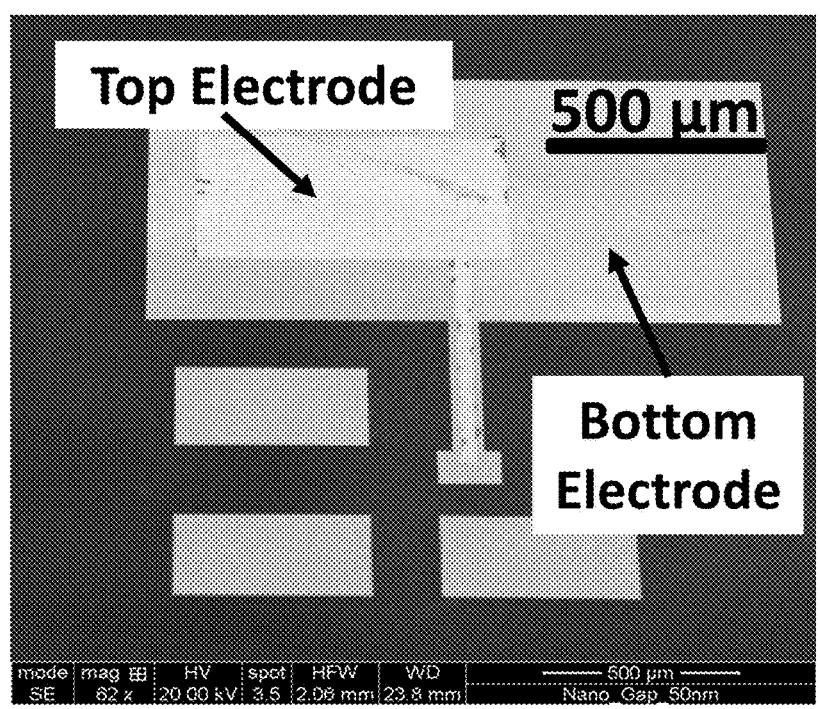
FIG. 20B is an SEM image of the top and bottom electrodes shown in FIG. 20A.

FIG. 20A is an SEM image of a nano-gap with a gap distance of 50 nm in a switch for detecting proteins. FIG. 20B is an SEM image of the top and bottom electrodes of the same switch.

Figure 21:
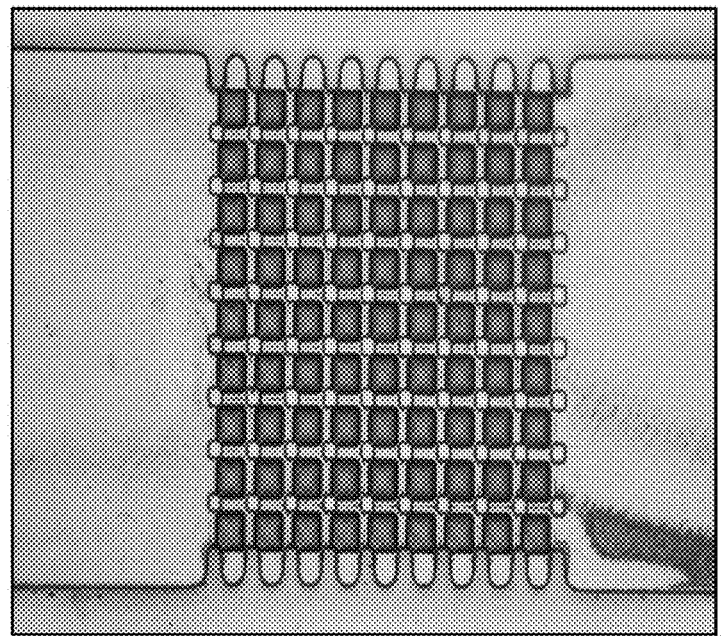
FIG. 21 is an SEM image of a chemically-selective percolation switch, in accordance with examples of the present invention.

FIG. 21 is an SEM image of a chemically-selective percolation switch having an array of square-shaped overlapping parallel horizontal plates forming a corresponding matrix of vertical structure gaps in the horizontal switch gap (similar to FIG. 6A).

Figure 22:
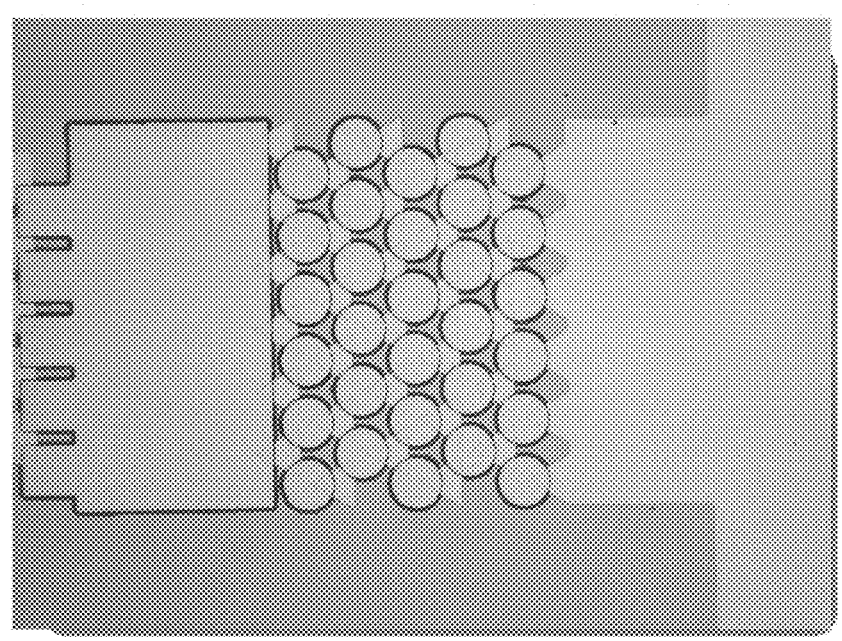
FIG. 22 is an SEM image of a chemically-selective percolation switch, in accordance with examples of the present invention.

FIG. 22 is an SEM image of a chemically-selective percolation switch having an array of triangular and circular overlapping parallel horizontal plates forming a matrix of structure gaps in the switch gap (similar to FIG. 7).

Figure 23:
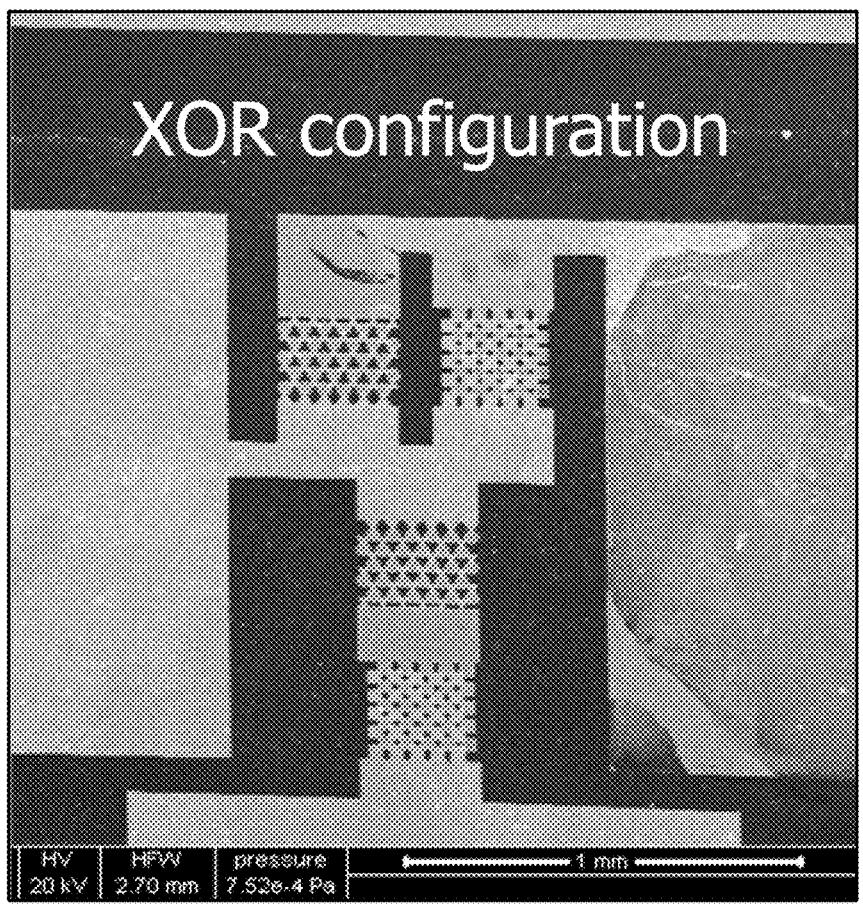
FIG. 23 is an SEM image of a XOR type functioning circuit element by utilizing several chemically-selective percolation switches, in accordance with examples of the present invention.

FIG. 23 is an SEM image of a XOR type circuit element including four chemically-selective percolation switches having either square-shaped overlapping parallel horizontal plates or circular and triangular overlapping parallel horizontal plates. The upper two switches are electrically arranged in parallel while the lower two switches are arranged in series. Any combination of such logic gates can also be used to result in true/false signals. For example, multiple chemically-selective percolation switches can be oriented in series, parallel, or combinations thereof to form a logic circuit (e.g. AND, OR, NOT, NAND, NOR, XOR, EXOR, EXNOR, and the like).

Figure 24:
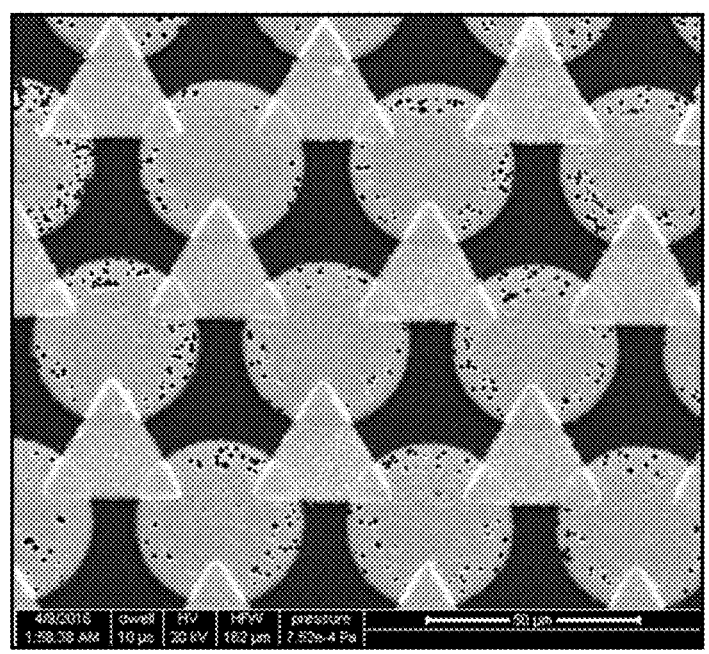
FIG. 24 is an SEM image of circular and triangular overlapping parallel horizontal plates.

FIG. 24 is a close-up SEM image of the circular and triangular overlapping parallel horizontal plates of FIG. 23.

Figure 25:
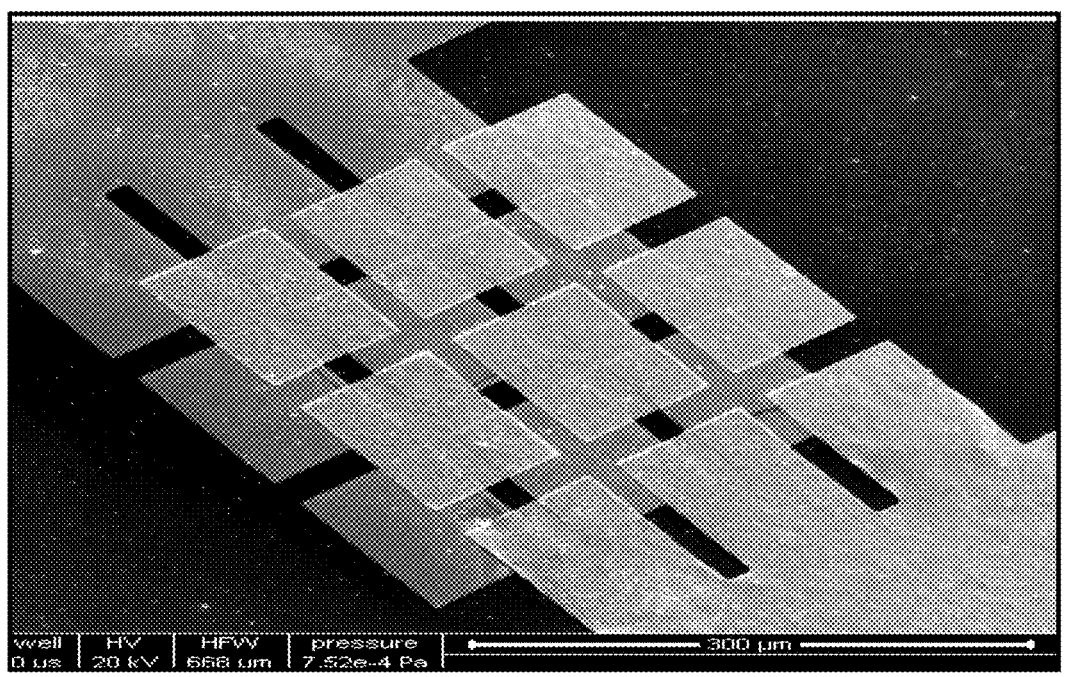
FIG. 25 is an SEM image of a chemically-selective percolation switch, in accordance with examples of the present invention.

FIG. 25 is an SEM image of another chemically-selective percolation switch having square-shaped overlapping parallel horizontal plates in the switch gap.

Figure 26A:
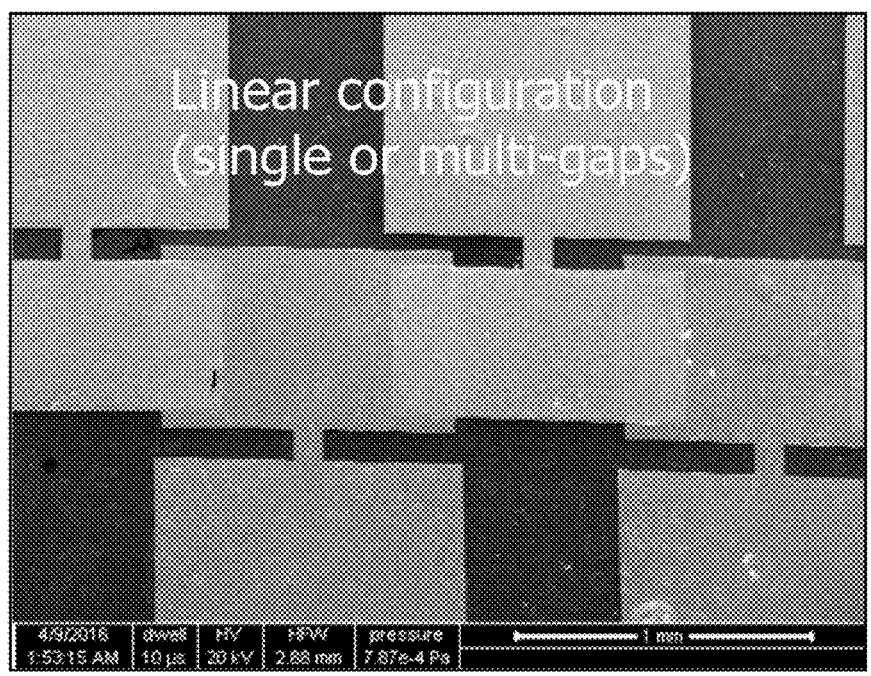
FIG. 26A is an SEM image of a chemically-selective percolation switch, in accordance with examples of the present invention.
Figure 26B:
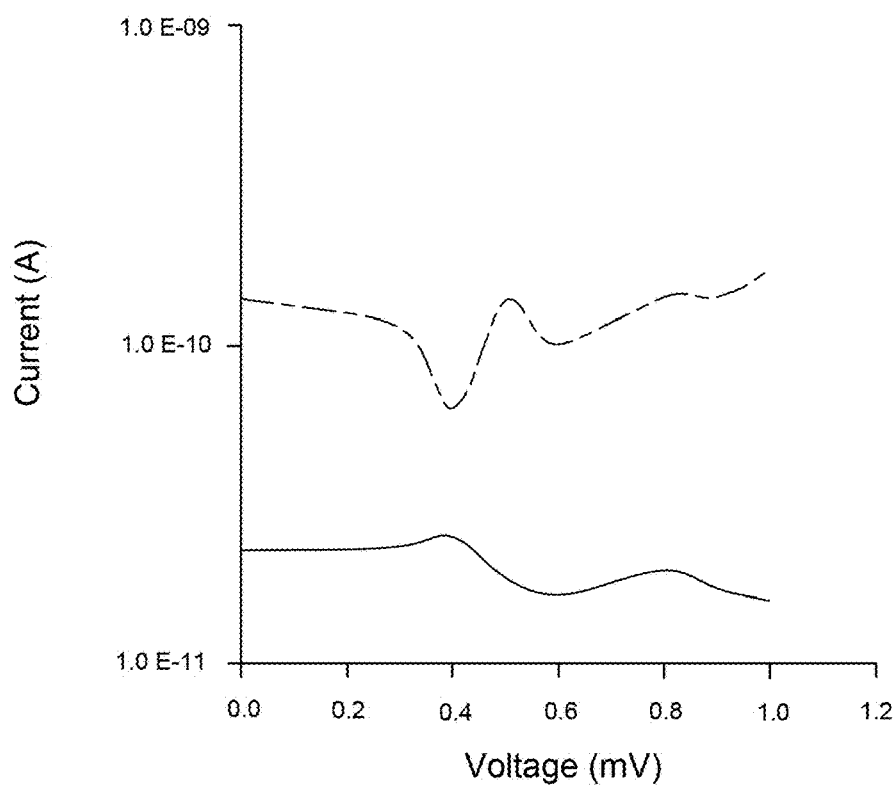
FIG. 26B is a graph of current vs. voltage for the chemically-selective percolation switch of FIG. 26A.

FIG. 26A is an SEM image of another chemically-selective percolation switch having rectangular parallel horizontal plates overlapping in a linear pattern. The gap distance of this switch was 6 nanometers. This switch was configured to detect 1,5-diaminopentane as the target compound. The switch was tested by cycling voltages 0.0 mV to 1.0 mV with and without the presence of 1,5-diaminopentane. FIG. 26B is a graph of current vs. voltage with the solid line showing the test results without 1,5-diaminopentane and the dashed line showing the test results with the 1,5-diaminopentane. The current increased from approximately $10^{-11}$ A to approximately $10^{-10}$ A, or an increase of ten-fold.

Figure 27A:
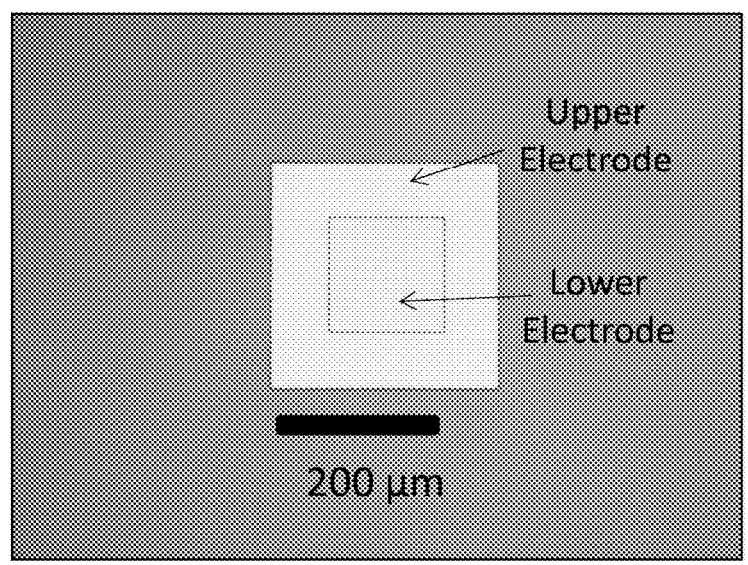
FIG. 27A is a schematic drawing of a chemically-selective percolation switch, in accordance with examples of the present invention.
Figure 27B:
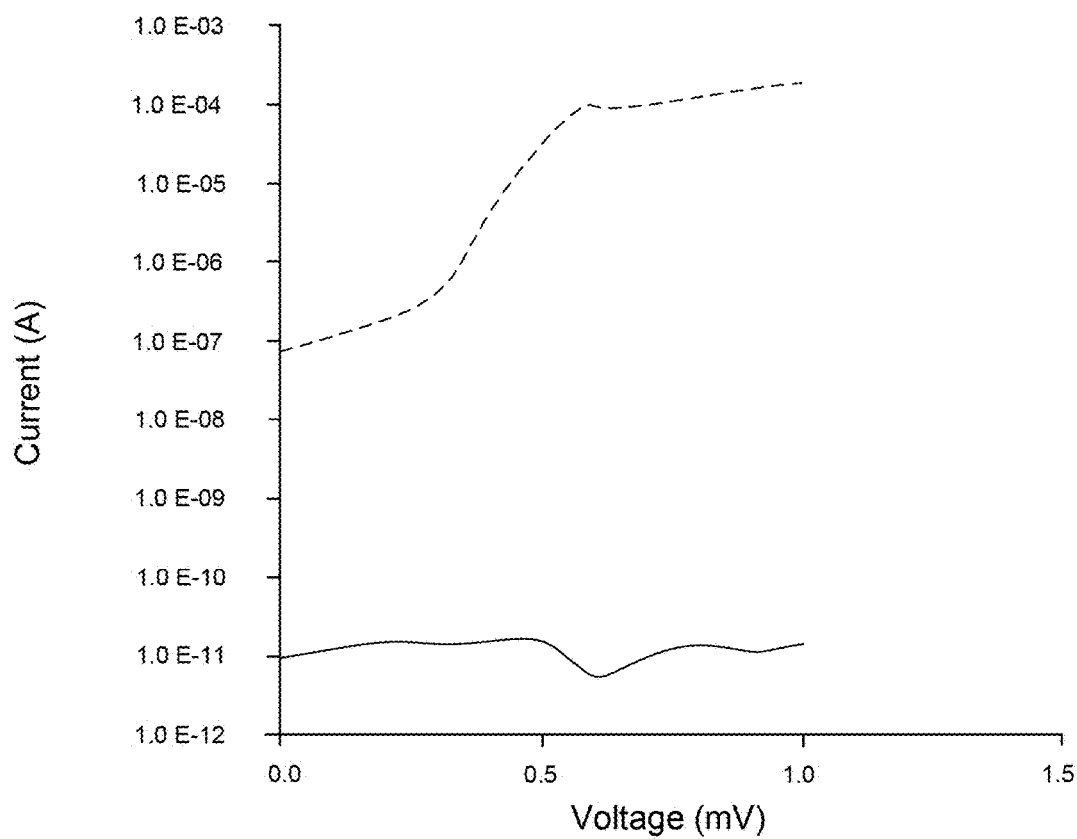
FIG. 27B is a graph of current vs. voltage for the chemically-selective percolation switch of FIG. 27A.
Figure 27C:
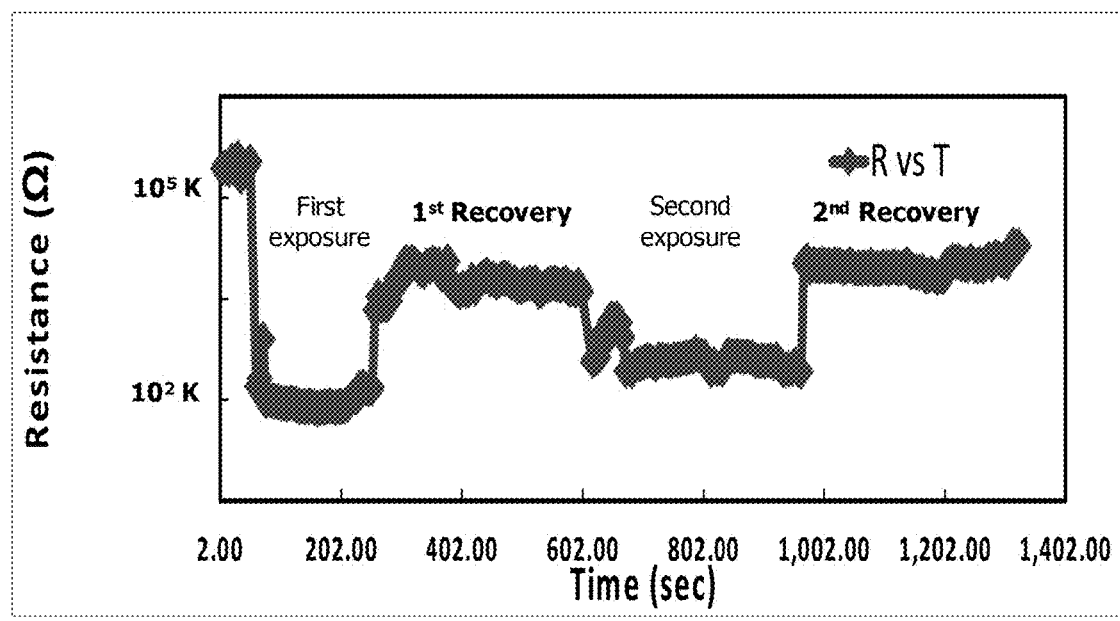
FIG. 27C is a graph of resistance over time while exposing the chemically-selective percolation switch of FIG. 27A to a target compound.

FIG. 27A is a schematic drawing of a chemically-selective percolation switch having square-shaped overlapping parallel horizontal plates. The switch was designed with to detect 1,5-diaminopentane as the target compound, with a threshold concentration of approximately 796 ppm. The gap distance between the parallel plates was 6 nanometers. This switch was tested by cycling voltages from 0.0 to 1.0 mV and measuring the current across the switch. The test was performed in an atmosphere devoid of 1,5-diaminopentane. FIG. 27B is a graph of current vs. voltage measured during the test. The solid line shows the results of the test without 1,5-diaminopentane. The test was performed again with 1,5-diaminopentane present. The results of the test with 1,5-diaminopentane are shown as the dashed line. The current measured with the 1,5-diaminopentane present was up to about $10^7$ times greater than without the 1,5-diaminopentane. Another test was performed by measuring the resistance of the switch while exposing the switch to 1,5-diaminopentane, then recovering the 1,5-diaminopentane, then exposing the switch to 1,5-diaminopentane a second time, and then recovering the 1,5-diaminopentane a second time. The resistance vs. time during this test is shown FIG. 27C. The resistance of the switch was reduced each time the 1,5-diaminopentane was introduced, showing that the percolation process is reversible and can be used multiple times.

The described features, structures, or characteristics may be combined in any suitable manner in one or more examples. In the preceding description numerous specific details were provided, such as examples of various configurations to provide a thorough understanding of examples of the described technology. One skilled in the relevant art will recognize, however, that the technology may be practiced without one or more of the specific details, or with other methods, components, devices, etc. In other instances, well-known structures or operations are not shown or described in detail to avoid obscuring aspects of the technology.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A chemically-selective percolation switch, comprising:
    a positive electrode;
    a negative electrode separated from the positive electrode by a horizontal switch gap;
    a plurality of electrically conductive horizontal parallel plates formed in the switch gap, wherein at least some of the horizontal parallel plates vertically overlap at least some other horizontal parallel plates to form vertical structure gaps; and
    a binding agent located at a plurality of binding sites in the switch gap, wherein the binding agent is selective for binding to a target chemical compound, wherein the binding sites are on horizontal surfaces of the horizontal parallel plates, wherein the binding sites are distributed in the switch gap such that the binding sites are capable of binding molecules of the target chemical compound to form an electrically conductive pathway via percolation between the positive electrode and the negative electrode when the chemically-selective percolation switch is exposed to a threshold concentration of the target chemical compound.

2. The chemically-selective percolation switch of claim 1, wherein the threshold concentration can be adjusted from 1 part per billion (ppb) to 1000 part per million (ppm).

3. The chemically-selective percolation switch of claim 1, wherein the target chemical compound is a chemical warfare agent, an air pollutant, an airborne compound, a fuel, an explosive, an airborne biological agent, or combinations thereof.

4. The chemically-selective percolation switch of claim 1, wherein the horizontal parallel plates have a shape selected from circular, hexagonal, square, rectangular, and triangular.

5. The chemically-selective percolation switch of claim 1, wherein the horizontal parallel plates have a width from 1 micrometer to 1 millimeter.

6. The chemically-selective percolation switch of claim 1, wherein the vertical structure gaps have a structure gap distance from 0.3 nanometer to 100 micrometers.

7. The chemically-selective percolation switch of claim 1, further comprising a power supply connected to the positive electrode and the negative electrode to apply a bias voltage to the positive electrode and the negative electrode.

8. The chemically-selective percolation switch of claim 1, wherein the binding agent comprises a selective binding material.

9. The chemically-selective percolation switch of claim 1, wherein the plurality of electrically conductive horizontal parallel plates includes a first layer of horizontal plates in a same plane as the positive electrode and a second layer of horizontal plates in a same plane as the negative electrode, wherein the horizontal plates of the first layer vertically overlap the horizontal plates of the second layer.

10. The chemically-selective percolation switch of claim 1, wherein the plurality of electrically conductive horizontal parallel plates includes square plates vertically overlapping at corners of the square plates.

11. The chemically-selective percolation switch of claim 1, wherein the plurality of electrically conductive horizontal parallel plates includes a first layer of circular plates and a second layer of triangular plates, wherein the circulate plates vertically overlap the triangular plates at corners of the triangular plates.

12. The chemically-selective percolation switch of claim 1, wherein the plurality of electrically conductive horizontal parallel plates are organized as a linear row of vertically overlapping horizontal parallel plates.

13. A zero-power digital chemical analyzer, comprising:
a power supply;
a detection circuit; and
a chemically-selective percolation switch electrically connected between the power supply and the detection circuit, wherein the chemically-selective percolation switch is configured to switch the detection circuit to an on state when the chemically-selective percolation switch is exposed to a threshold concentration of a target chemical compound, and wherein the chemically-selective percolation switch comprises:
a positive electrode;
a negative electrode separated from the positive electrode by a horizontal switch gap;
a plurality of electrically conductive horizontal parallel plates formed in the switch gap, wherein at least some of the horizontal parallel plates vertically overlap at least some other horizontal parallel plates to form vertical structure gaps; and
a binding agent located at a plurality of binding sites in the switch gap, wherein the binding agent is selective for binding to the target chemical compound, wherein the binding sites are on horizontal surfaces of the horizontal parallel plates, wherein the binding sites are distributed in the switch gap such that the binding sites are capable of binding molecules of the target chemical compound to form an electrically conductive pathway via percolation between the positive electrode and the negative electrode when the chemically-selective percolation switch is exposed to the threshold concentration of the target chemical compound.

14. The zero-power digital chemical analyzer of claim 13, further comprising a charging capacitor electrically connected between the chemically-selective percolation switch and the detection circuit.

15. The zero-power digital chemical analyzer of claim 13, wherein the chemically-selective percolation switch conducts a trivial current of less than 1 pA when the chemically-selective percolation switch is exposed to a concentration of the target chemical compound below the threshold concentration, and conducts a significant amount of current of at least 1 nA when the chemically-selective percolation switch is exposed to the threshold concentration of the target chemical compound, forming an electrically-conductive path via the natural percolation phenomenon.

16. The zero-power digital chemical analyzer of claim 13, further comprising a second chemically-selective percolation switch connected in series with the chemically-selective percolation switch so that the detection circuit is not switched to the on state unless both the chemically-selective percolation switch and the second chemically-selective percolation switch conduct electric current from the power supply, wherein the second chemically-selective percolation switch is tuned to conduct electricity via the natural percolation phenomenon when exposed to the same threshold concentration of the target chemical compound as the chemically-selective percolation switch.

17. The zero-power digital chemical analyzer of claim 13, further comprising a second chemically-selective percolation switch connected in series with the chemically-selective percolation switch and an additional pair of chemically-selective percolation switches connected in parallel one with another, wherein the additional pair of chemically-selective percolation switches is connected in series with the first and second chemically selective percolation switches to form an XOR logic gate.

18. A digital chemical analyzer, comprising:
a power supply;
a first chemically-selective percolation switch tuned to conduct electric current from the power supply when exposed to a first threshold concentration of a target chemical compound; and
a second chemically-selective percolation switch tuned to conduct electric current when exposed to a second threshold concentration of the target chemical compound, wherein the second threshold concentration is greater than the first threshold concentration;

wherein the first and second chemically-selective percolation switches each comprise:
a positive electrode;
a negative electrode separated from the positive electrode by a horizontal switch gap;
a plurality of electrically conductive horizontal parallel plates formed in the switch gap, wherein at least some of the horizontal parallel plates vertically overlap at least some other horizontal parallel plates to form vertical structure gaps; and
a binding agent located at a plurality of binding sites in the switch gap, wherein the binding agent is selective for binding to the target chemical compound, wherein the binding sites are on horizontal surfaces of the horizontal parallel plates, wherein the binding sites are distributed in the switch gap such that the binding sites are capable of binding molecules of the target chemical compound to form an electrically conductive pathway via percolation between the positive electrode and the negative electrode when the chemically-selective percolation switch is exposed to the threshold concentration of the target chemical compound.

19. The digital chemical analyzer of claim 18, further comprising a detection circuit electrically connected to the first and second chemically-selective percolation switches, wherein the detection circuit is configured to determine a minimum ambient concentration of the target chemical compound based on signals from the first and second chemically-selective percolation switches.

20. The digital chemical analyzer of claim 18, wherein the first and second chemically-selective percolation switches are tuned to the first and second threshold concentrations by adjusting one or more of a bias voltage, binding agent, binding agent concentration, switch gap distance between electrodes, distance between electrically conductive structures in the switch gap, surface area of electrically conductive structures in the switch gap, height of electrically conductive structures in the switch gap, or combinations thereof.

* * * * *

UNITED STATES PATENT AND TRADEMARK OFFICE
CERTIFICATE OF CORRECTION

| | | |
|---|---|---|
| PATENT NO. | : 10,502,724 B2 | Page 1 of 1 |
| APPLICATION NO. | : 15/376562 | |
| DATED | : December 10, 2019 | |
| INVENTOR(S) | : Kim et al. | |

It is certified that error appears in the above-identified patent and that said Letters Patent is hereby corrected as shown below:

In the Specification

Column 1 Line 12, Insert new paragraph:
--This invention was made with government support under grant awarded by Defense Advanced Research Projects Agency. The government has certain rights in this invention.--

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*